(12) United States Patent
Adzich et al.

(10) Patent No.: US 7,842,085 B2
(45) Date of Patent: Nov. 30, 2010

(54) ANNULOPLASTY RING AND HOLDER COMBINATION

(76) Inventors: Vaso Adzich, 19102 Kassy Dr., Santa Ana, CA (US) 92705; Aaron Ingle, 38 Abrazo Aisle, Irvine, CA (US) 92614; Matthew Winston, 35 Brisa Del Lago, Rancho Santa Margarita, CA (US) 92688

( * ) Notice: Subject to any disclaimer, the term of this patent is extended or adjusted under 35 U.S.C. 154(b) by 1125 days.

(21) Appl. No.: 11/515,466

(22) Filed: Sep. 1, 2006

(65) Prior Publication Data
US 2007/0156234 A1 Jul. 5, 2007

Related U.S. Application Data

(63) Continuation-in-part of application No. 11/386,429, filed on Mar. 22, 2006, now Pat. No. 7,575,595.

(60) Provisional application No. 60/664,875, filed on Mar. 23, 2005.

(51) Int. Cl.
*A61F 2/24* (2006.01)
(52) U.S. Cl. .................................. 623/2.36; 623/2.11
(58) Field of Classification Search ............... 623/2.11, 623/2.36, 2.37
See application file for complete search history.

(56) References Cited

U.S. PATENT DOCUMENTS

| | | | |
|---|---|---|---|
| 3,656,185 A | 4/1972 | Carpentier | |
| 4,055,861 A | 11/1977 | Carpentier et al. | |
| 4,164,046 A | 8/1979 | Cooley | |
| 4,217,665 A | 8/1980 | Bex et al. | |
| 4,602,911 A | 7/1986 | Ahmadi et al. | |
| 5,041,130 A | 8/1991 | Cosgrove et al. | |
| 5,061,277 A | 10/1991 | Carpentier et al. | |
| 5,064,431 A | 11/1991 | Gilbertson et al. | |
| 5,104,407 A | 4/1992 | Lam et al. | |
| 5,201,880 A | 4/1993 | Wright et al. | |
| 5,258,021 A | 11/1993 | Duran | |

(Continued)

FOREIGN PATENT DOCUMENTS

EP 0 338 994 10/1989

(Continued)

OTHER PUBLICATIONS

International Search Report for Application No. PCT/US2007/076676, dated Jul. 1, 2008.

(Continued)

*Primary Examiner*—Bruce E Snow
(74) *Attorney, Agent, or Firm*—AnneMarie Kaiser

(57) ABSTRACT

An annuloplasty ring and ring holder combination includes a generally triangular-shaped ring and a generally T-shaped holder. The ring holder has a base portion forming the top of the T shape and engaging against a first segment of the ring, with a radial arm extending from the base portion and forming the post of the T. The radial arm engages against a junction between two segments of the ring. The invention includes placements of suture holes and cutting wells which, in combination with the improved ring holder shape, afford the user improved access and visibility to the surgical site, the ring, and to the suture that is used to retain the annuloplasty ring to the holder.

20 Claims, 20 Drawing Sheets

U.S. PATENT DOCUMENTS

| | | | |
|---|---|---|---|
| 5,306,296 | A | 4/1994 | Wright et al. |
| 5,450,860 | A | 9/1995 | Seguin et al. |
| 5,496,336 | A | 3/1996 | Cosgrove et al. |
| 5,593,435 | A | 1/1997 | Carpentier et al. |
| 5,607,471 | A | 3/1997 | Seguin et al. |
| 5,674,279 | A | 10/1997 | Wright et al. |
| 5,683,402 | A | 11/1997 | Cosgrove |
| 5,776,189 | A | 7/1998 | Khalid |
| 5,824,066 | A | 10/1998 | Gross |
| 5,824,069 | A | 10/1998 | Lemole |
| 5,888,240 | A | 3/1999 | Carpentier et al. |
| 5,972,030 | A | 10/1999 | Garrison et al. |
| 6,019,739 | A | 2/2000 | Rhee et al. |
| 6,024,918 | A | 2/2000 | Hendriks et al. |
| 6,102,945 | A | 8/2000 | Campbell |
| 6,143,024 | A | 11/2000 | Campbell et al. |
| 6,159,240 | A | 12/2000 | Sparer et al. |
| 6,183,512 | B1 | 2/2001 | Howanec, Jr. et al. |
| 6,187,040 | B1 | 2/2001 | Wright |
| 6,217,610 | B1 | 4/2001 | Carpentier et al. |
| 6,231,602 | B1 | 5/2001 | Carpentier et al. |
| 6,250,308 | B1 | 6/2001 | Cox |
| 6,258,122 | B1 | 7/2001 | Tweden et al. |
| 6,391,054 | B2 | 5/2002 | Carpentier et al. |
| 6,406,493 | B1 | 6/2002 | Tu et al. |
| 6,419,696 | B1 | 7/2002 | Ortiz et al. |
| 6,602,288 | B1 | 8/2003 | Cosgrove et al. |
| 6,602,289 | B1 | 8/2003 | Colvin et al. |
| 6,619,291 | B2 | 9/2003 | Hlavka et al. |
| 6,709,456 | B2 | 3/2004 | Langberg et al. |
| 6,718,985 | B2 | 4/2004 | Hlavka et al. |
| 6,719,786 | B2 | 4/2004 | Ryan et al. |
| 6,726,717 | B2 | 4/2004 | Alfeiri et al. |
| 6,749,630 | B2 | 6/2004 | McCarthy et al. |
| 6,797,002 | B2 | 9/2004 | Spence et al. |
| 6,800,090 | B2 | 10/2004 | Alferness et al. |
| 6,802,860 | B2 | 10/2004 | Cosgrove et al. |
| 6,805,710 | B2 | 10/2004 | Bolling et al. |
| 6,858,039 | B2 | 2/2005 | McCarthy |
| 6,908,482 | B2 | 6/2005 | McCarthy et al. |
| 6,918,917 | B1 | 7/2005 | Nguyen et al. |
| 6,921,407 | B2 | 7/2005 | Nguyen et al. |
| 6,942,694 | B2 | 9/2005 | Liddicoat et al. |
| 6,955,689 | B2 | 10/2005 | Ryan et al. |
| 6,966,924 | B2 | 11/2005 | Holmberg |
| 6,986,775 | B2 | 1/2006 | Morales et al. |
| 7,037,334 | B1 | 5/2006 | Hlavka et al. |
| 7,066,954 | B2 | 6/2006 | Ryan et al. |
| 7,118,595 | B2 | 10/2006 | Ryan et al. |
| 7,125,421 | B2 | 10/2006 | Tremulis et al. |
| 7,166,126 | B2 | 1/2007 | Spence et al. |
| 7,166,127 | B2 | 1/2007 | Spence et al. |
| 7,294,148 | B2 | 11/2007 | McCarthy |
| 7,329,280 | B2 | 2/2008 | Bolling et al. |
| 2001/0034551 | A1 | 10/2001 | Cox |
| 2002/0129820 | A1 | 9/2002 | Ryan et al. |
| 2002/0133180 | A1 | 9/2002 | Ryan et al. |
| 2002/0169504 | A1 | 11/2002 | Alferness et al. |
| 2002/0173844 | A1 | 11/2002 | Alfieri et al. |
| 2003/0033009 | A1 | 2/2003 | Gabbay |
| 2003/0040793 | A1 | 2/2003 | Marquez |
| 2003/0083742 | A1 | 5/2003 | Spence et al. |
| 2003/0093148 | A1 | 5/2003 | Bolling et al. |
| 2003/0125715 | A1* | 7/2003 | Kuehn et al. ............ 606/1 |
| 2004/0006384 | A1 | 1/2004 | McCarthy |
| 2004/0249452 | A1 | 12/2004 | Adams et al. |
| 2004/0249453 | A1 | 12/2004 | Cartledge et al. |
| 2005/0004666 | A1 | 1/2005 | Alfieri |
| 2005/0043791 | A1 | 2/2005 | McCarthy et al. |
| 2005/0131533 | A1 | 6/2005 | Alfieri et al. |
| 2005/0182487 | A1 | 8/2005 | McCarthy et al. |
| 2005/0192666 | A1 | 9/2005 | McCarthy |
| 2005/0197696 | A1 | 9/2005 | Gomez Duran |
| 2005/0246014 | A1 | 11/2005 | McCarthy |
| 2005/0256567 | A1 | 11/2005 | Lim et al. |
| 2005/0256568 | A1 | 11/2005 | Lim et al. |
| 2005/0256569 | A1 | 11/2005 | Lim et al. |
| 2005/0267572 | A1 | 12/2005 | Schoon |
| 2005/0278022 | A1 | 12/2005 | Lim |
| 2005/0288776 | A1 | 12/2005 | Shaoulian et al. |
| 2005/0288777 | A1 | 12/2005 | Rhee et al. |
| 2005/0288778 | A1 | 12/2005 | Shaoulian et al. |
| 2005/0288780 | A1 | 12/2005 | Rhee et al. |
| 2005/0288782 | A1 | 12/2005 | Moaddeb et al. |
| 2005/0288783 | A1 | 12/2005 | Shaoulian et al. |
| 2006/0015178 | A1 | 1/2006 | Moaddeb et al. |
| 2006/0015179 | A1 | 1/2006 | Bulman-Fleming et al. |
| 2006/0020336 | A1 | 1/2006 | Liddicoat |
| 2006/0025856 | A1 | 2/2006 | Ryan et al. |
| 2006/0025858 | A1 | 2/2006 | Alameddine |
| 2006/0030885 | A1 | 2/2006 | Hyde |
| 2008/0033545 | A1* | 2/2008 | Bergin ............ 623/2.11 |

FOREIGN PATENT DOCUMENTS

| | | |
|---|---|---|
| EP | 0 595 791 | 5/1994 |
| EP | 0 860 151 | 8/1998 |
| EP | 1 034 753 | 9/2000 |
| FR | 2 708 458 | 8/1993 |
| WO | WO 95/03757 | 2/1995 |
| WO | WO 01/19292 | 3/2001 |
| WO | WO 01/26586 | 4/2001 |
| WO | WO 01/47438 | 7/2001 |
| WO | WO 01/87191 | 11/2001 |
| WO | WO 02/03892 | 1/2002 |
| WO | WO 03/020178 | 3/2003 |
| WO | WO 03/041617 | 5/2003 |
| WO | WO 2004/004607 | 1/2004 |
| WO | WO 2005/034813 | 4/2005 |
| WO | WO 2005/110290 | 11/2005 |
| WO | WO 2006 102513 | 9/2006 |
| WO | WO 2007/050606 | 5/2007 |

OTHER PUBLICATIONS

Alonso-Lei, M.D., et al., Adjustable Annuloplasty for Tricuspid Insufficiency, The annals of Thoracic Surgery, vol. 46, No. 3, pp. 368-369, Sep. 1988.

Bolling, Mitral Valve Reconstruction in the Patient With Heart Failure, Heart Failure Reviews, 6, pp. 177-185, 2001.

Bolling, et al., Surgical Alternatives for Heart Failure, The Journal of Heart and Lung Transplantation, vol. 20, No. 7, pp. 729-733, 2001.

Carpentier-Edwards Classic Annuloplasty Ring With Duraflo Treatment Models 4425 and 4525 for Mitral and Tricuspid Valvuloplsty, Baxter Healthcare Corporation, 1998.

Carpentier-Edwards Pyshio Annuloplasty Ring, Edwards Lifesciences Corporation, 2003.

Cochran, et al., Effect of Papillary Muscle Position on Mitral Valve Function: Relationship to Homografts, The Society of Thoracic Surgeons, pp. 5165-5161, 1998.

D.C. Miller, IMR Redux- To Repair or Replace?, Journal of Thoracic & Cardiovascular Surgery, pp. 1-8, 2001.

Gatti, et al., Preliminary Experience in Mitral Valve Repair Using the Cosgrove-Edwards Annuloplasty Ring, Interactive Cardiovascular and Thoracic Surgery, vol. 2(3), pp. 256-261, 2003.

PCT International Search Report (PCT/US2004/032596) Mailed Jun. 20, 2005.

PCT International Search Report (PCT/US2005/014585) Mailed Sep. 29, 2005.

PCT International Search Report (PCT/US2005/020583) Mailed Oct. 11, 2005.

PCT International Search Report (PCT/US2006/001405) Mailed Jan. 13, 2006.

Melo, et al., Atrioventricular Valve Repair Using Externally Adjustable Flexible Rings: The Journal of Thoracic Cardiovascular Surgery, vol. 110, No. 5, 1995.

MGH Study Shows Mitral Valve Prolapse Not a Stroke Risk Factor, Massachusetts General Hospital, pp. 1-3, Jun. 1999.

Salgo, et al., Effect of Annular Shape on Leaflet Curvature in Reducing Mitral Leaflet, American Heart Association, Circulation 200; pp. 106-711.

Seguin, et al., Advance in Mitral Valve Repair Using a Device Flexible in Three Dimensions, The St. Jude Medical-Seguin Annuloplasty Ring, ASAIO Journal, vol. 42, No. 6, pp. 368-371, 1996.

Smolens, et al., Mitral Valve Repair in Heart Failure, The European Journal of Heart Failure 2, pp. 365-371, 2000.

Techniques for 3D Quantitative Echocardiography, University of Washington Cardiovascular Research & Training Center Cardiac Imaging Research Lab, pp. 1-5, Oct. 2003.

* cited by examiner

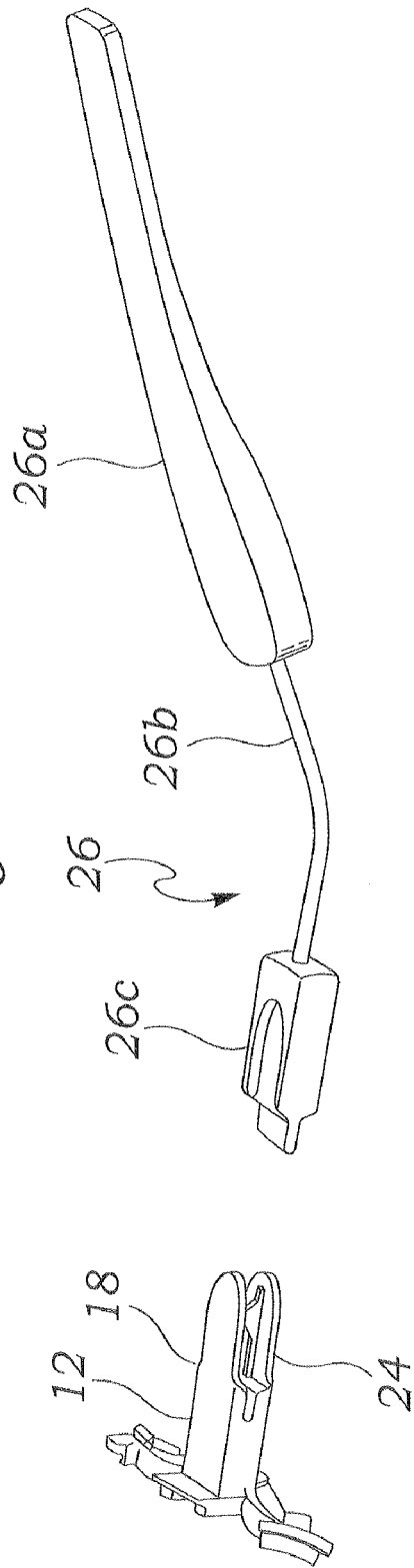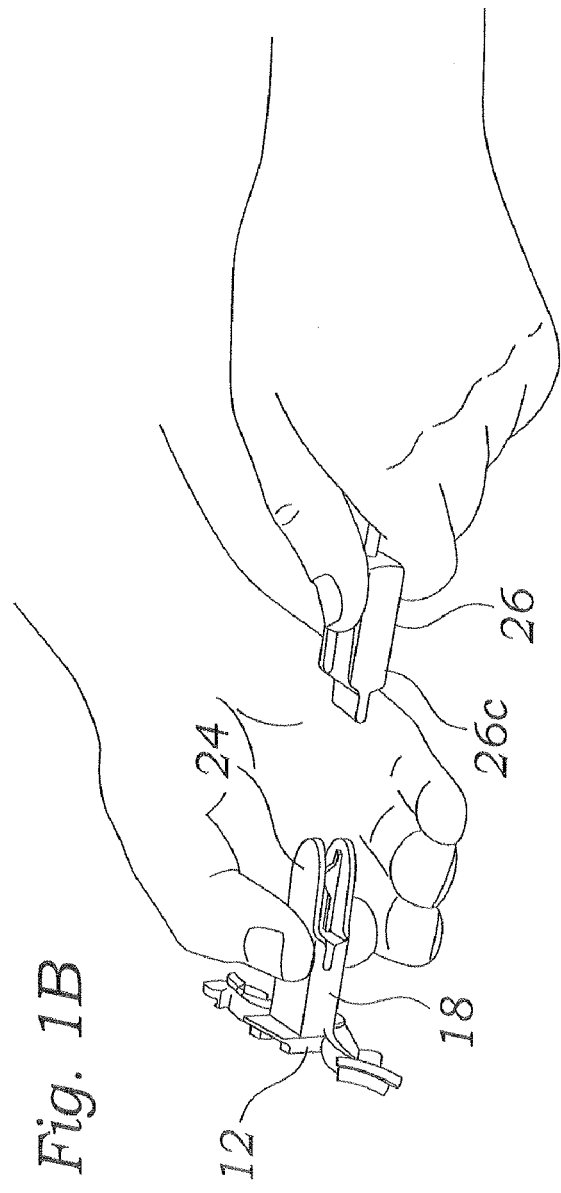

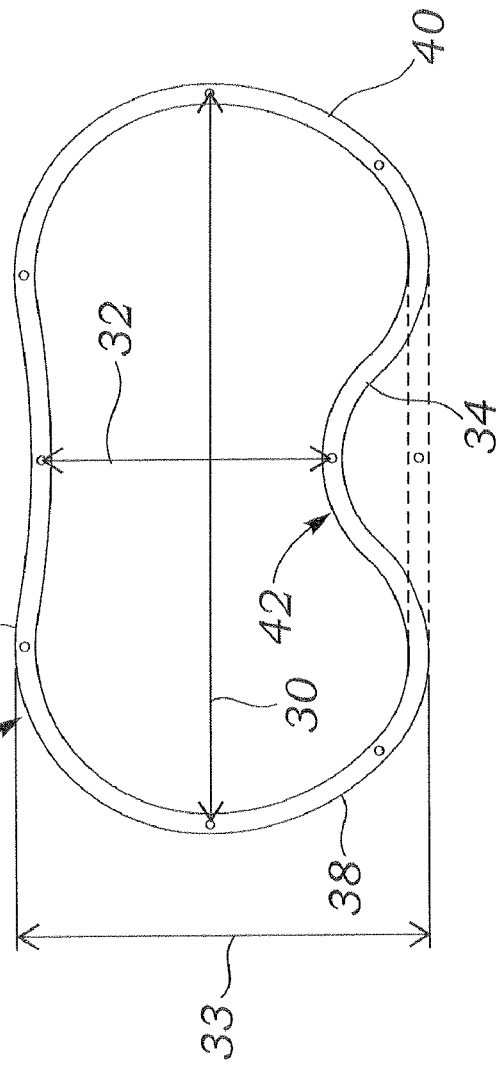
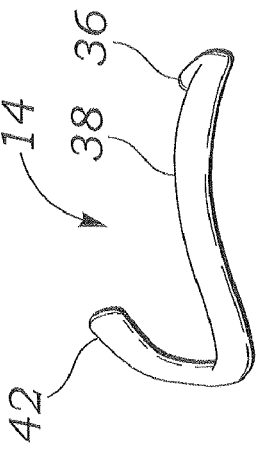
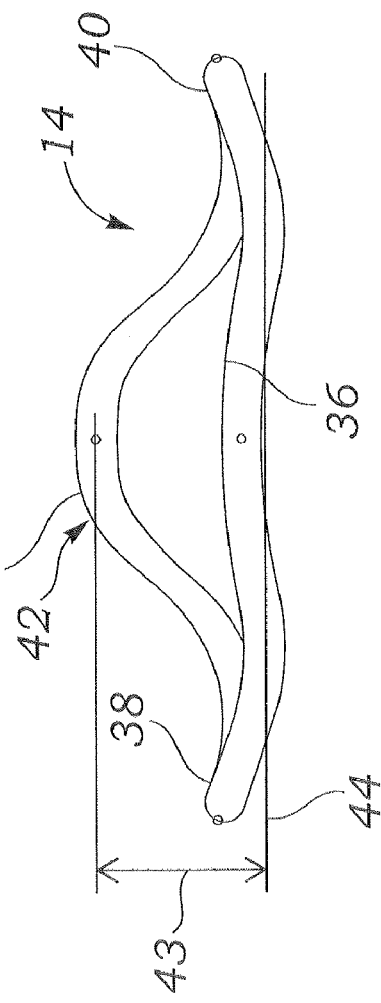

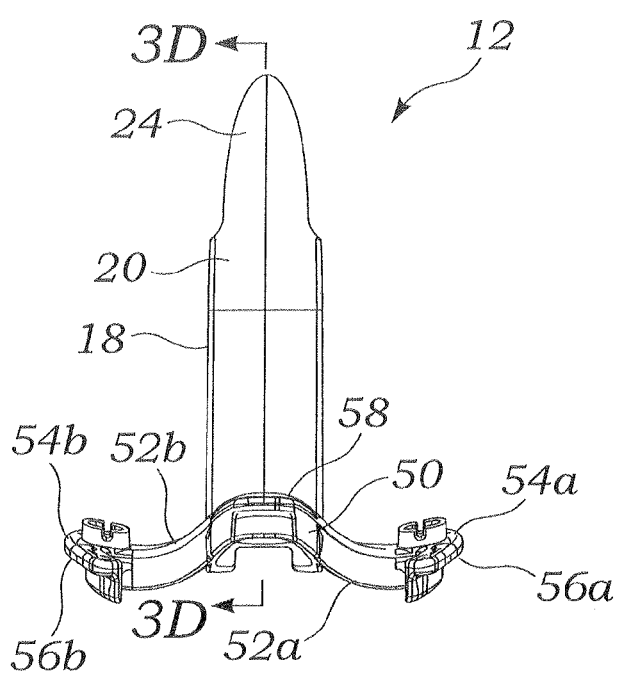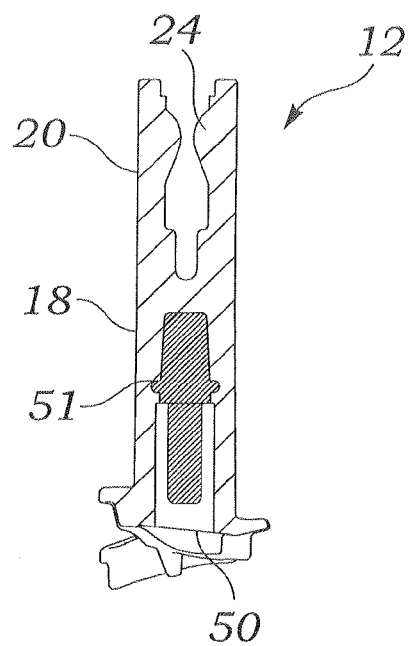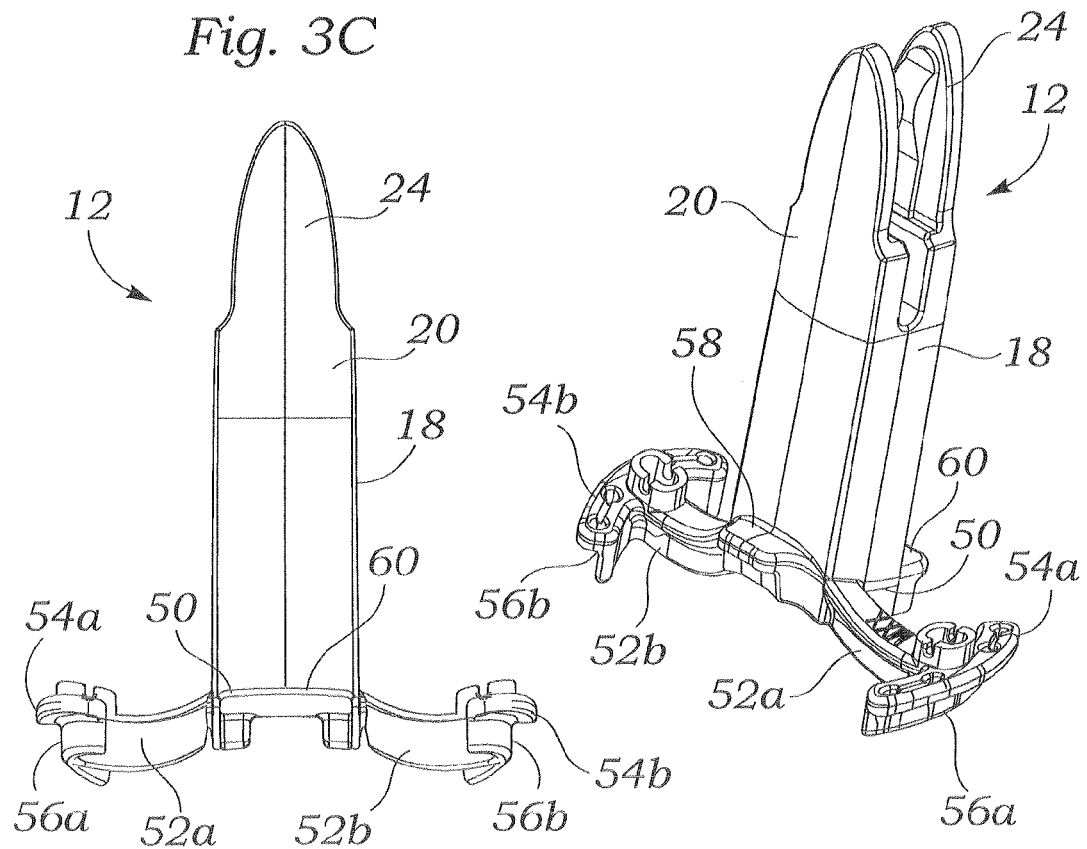

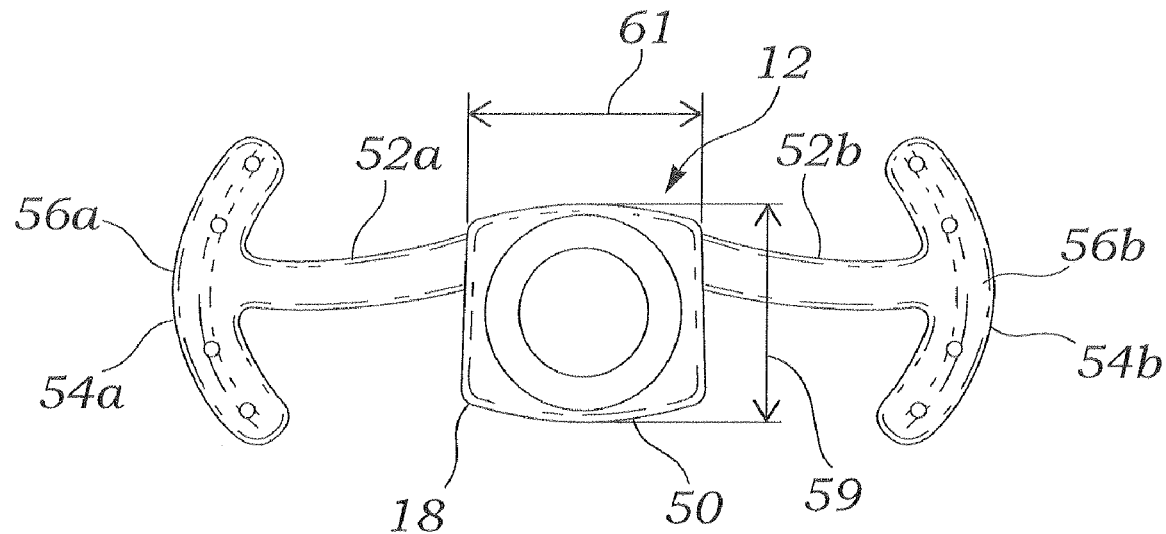
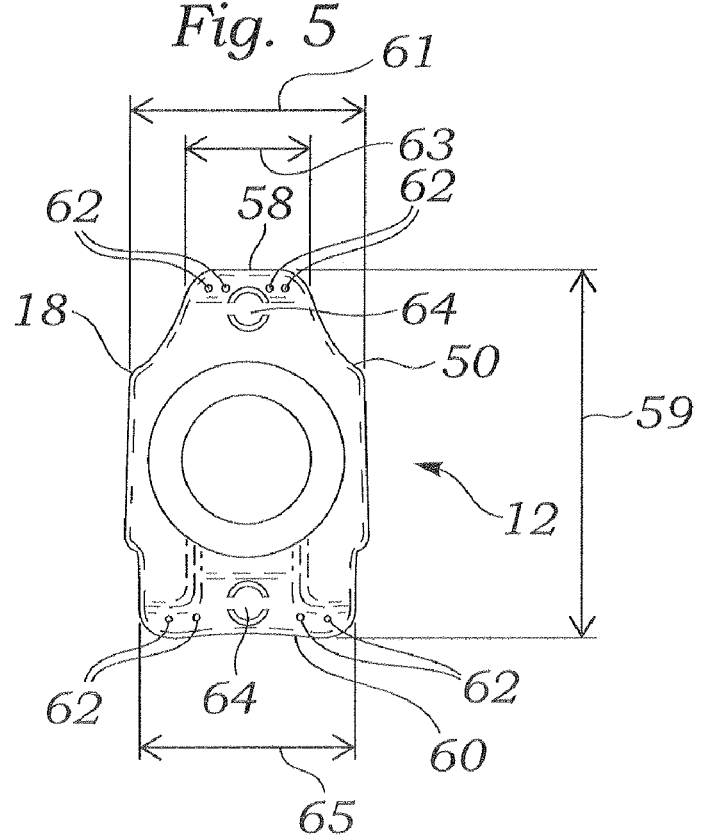

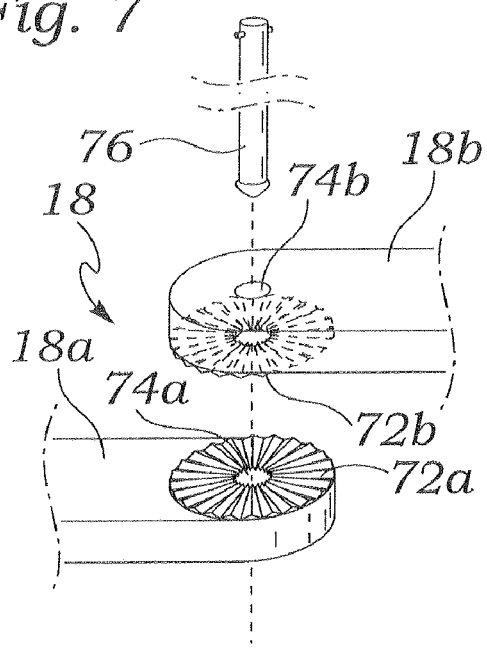
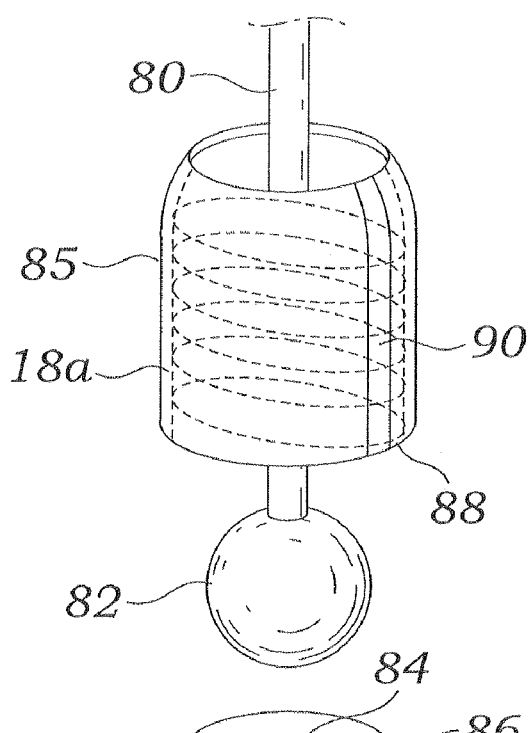
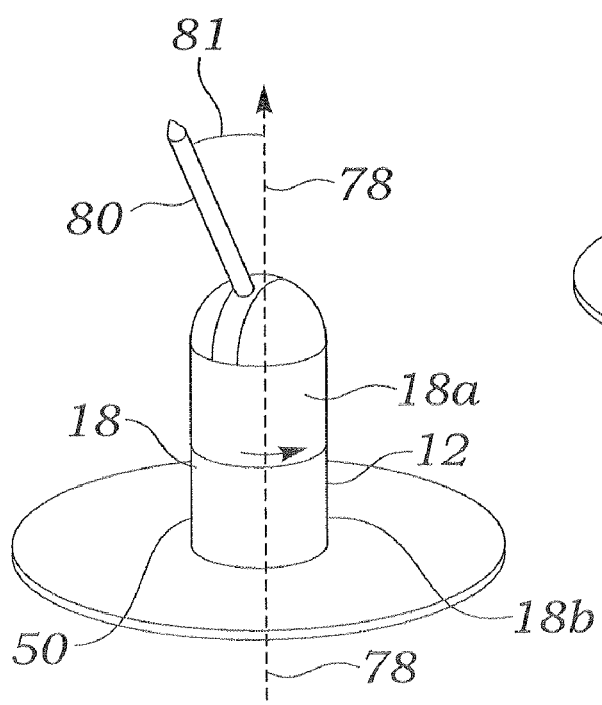

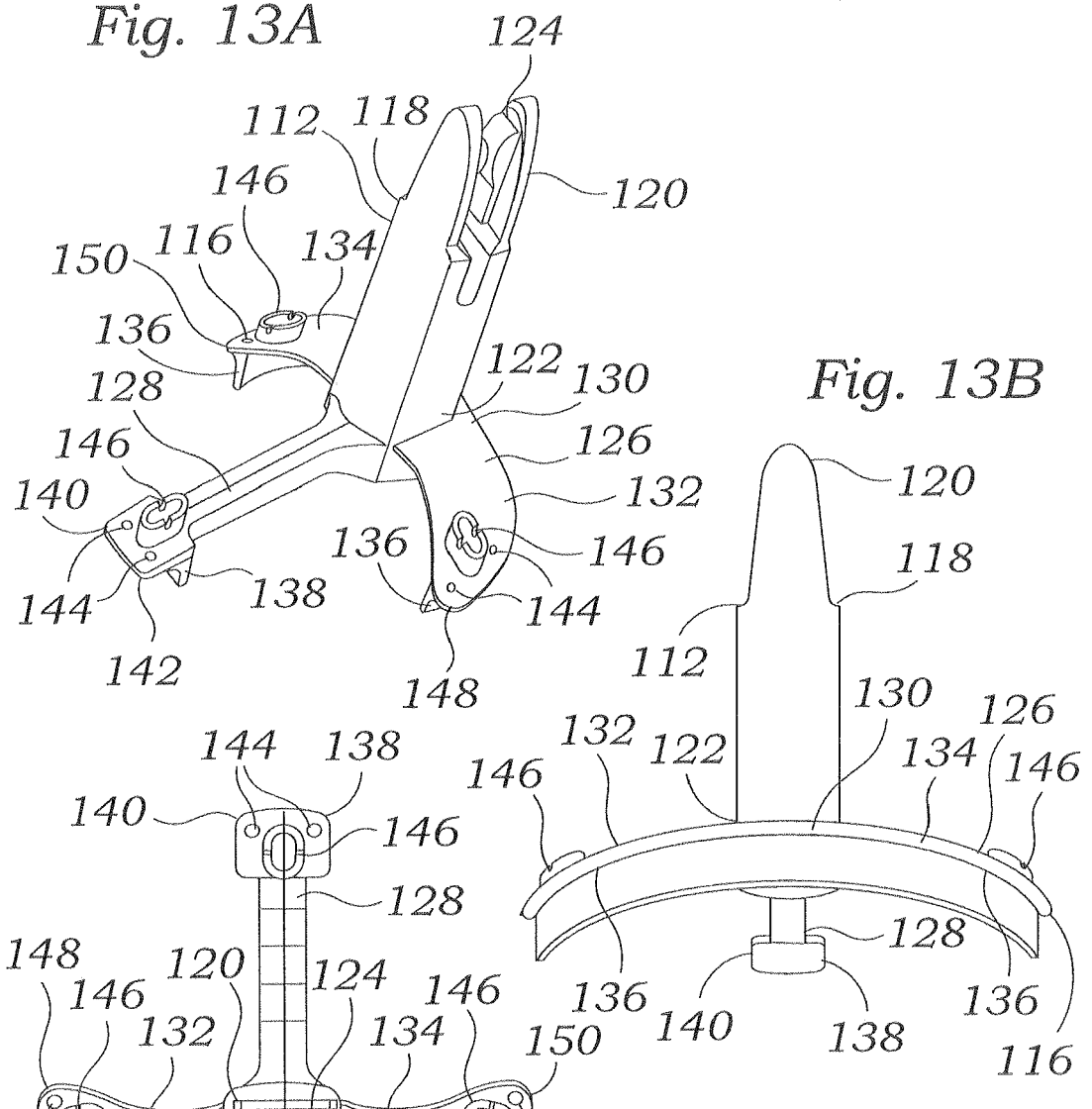
Fig. 13A
Fig. 13B
Fig. 13C
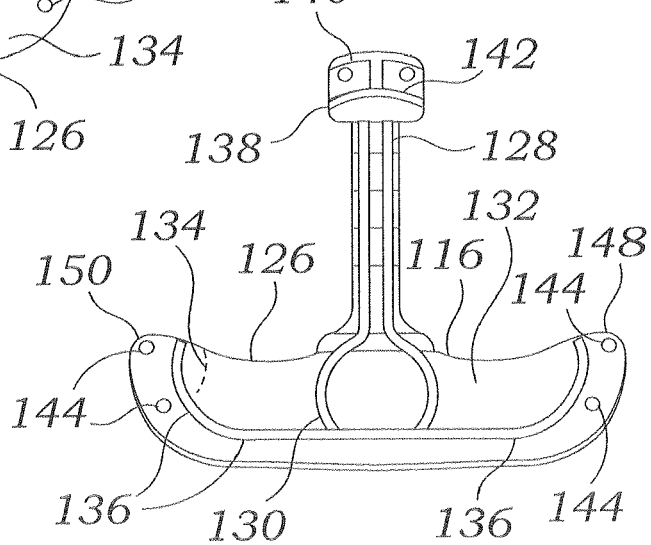
Fig. 13D

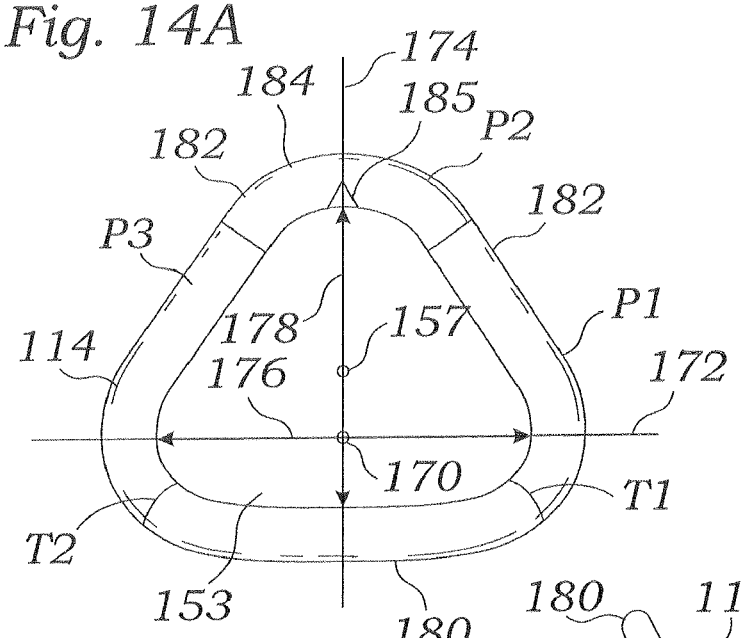
Fig. 14A
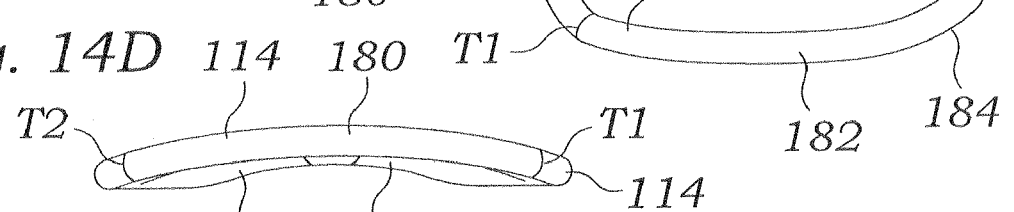
Fig. 14E
Fig. 14D
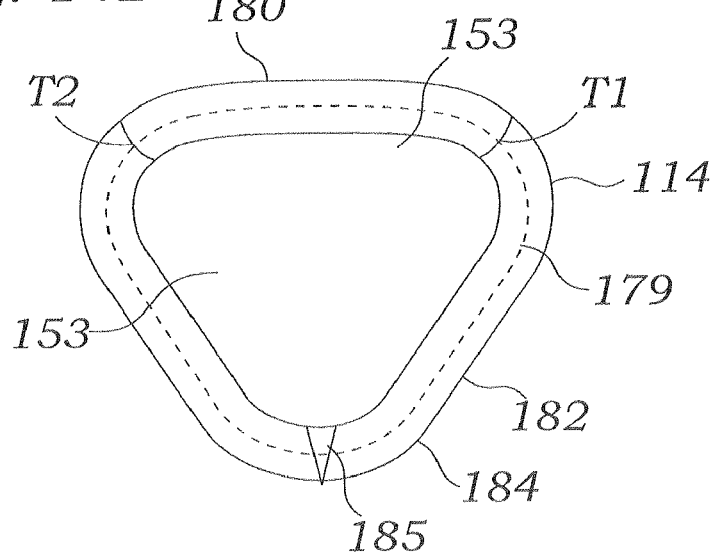
Fig. 14B
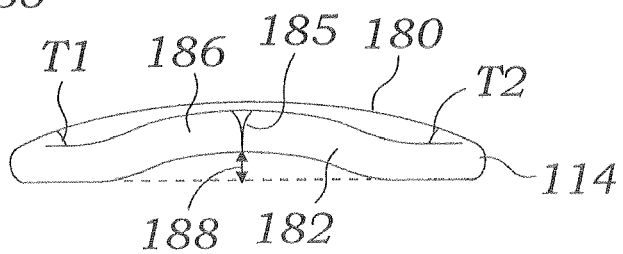
Fig. 14C

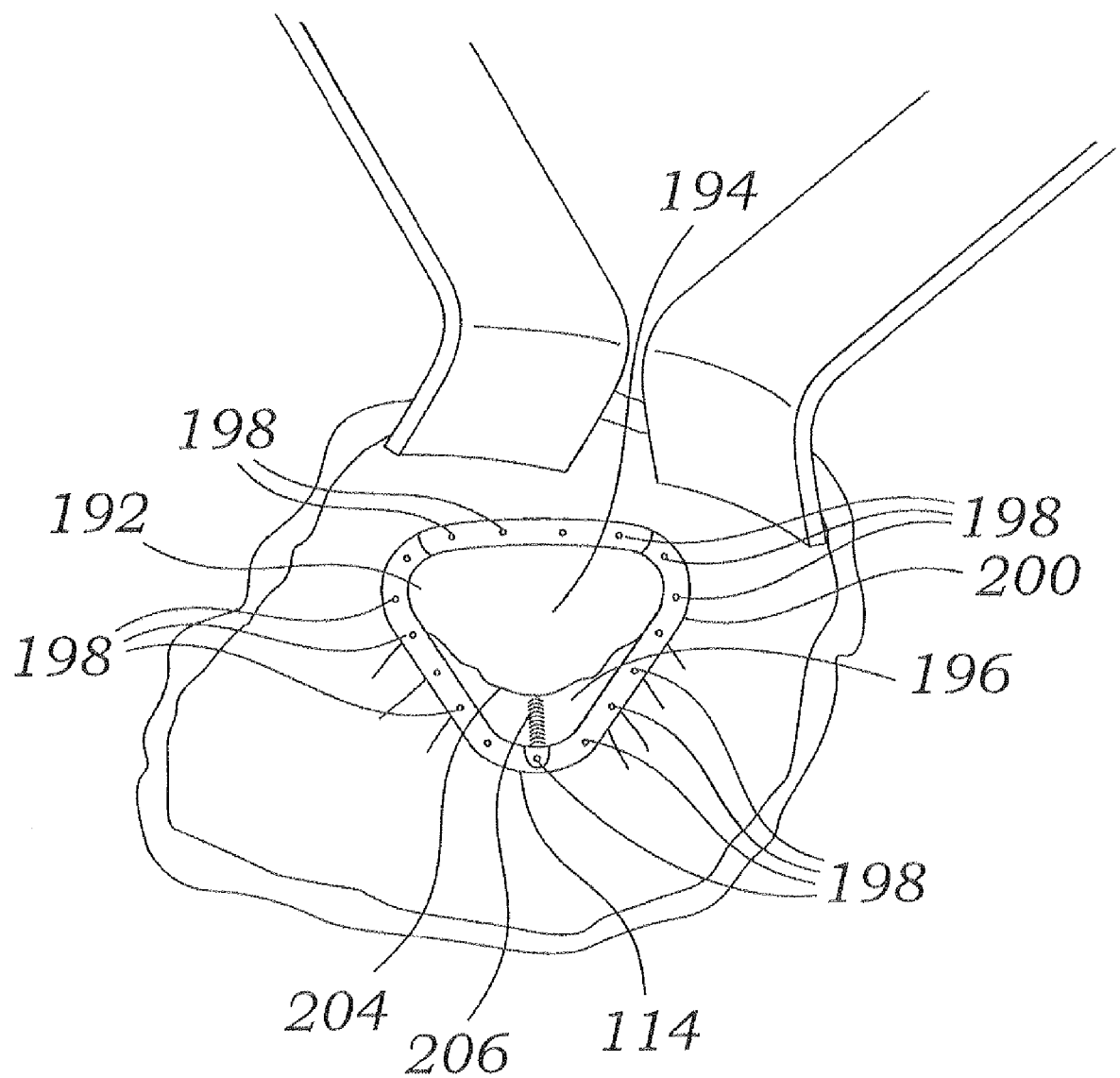

ANNULOPLASTY RING AND HOLDER COMBINATION

RELATED APPLICATIONS

This application is a continuation-in-part application from U.S. patent application Ser. No. 11/386,429, filed on Mar. 22, 2006, now U.S. Pat. No. 7,575,595, which claims priority from U.S. Provisional Application Ser. No. 60/664,875, filed on Mar. 23, 2005, the contents of which are expressly incorporated herein in their entirety. This application is related to U.S. patent Publication No. 2008/0058924, entitled "Saddle-Shaped Annuloplasty Ring" and filed concurrently herewith, the contents of which are expressly incorporated herein in their entirety.

FIELD OF THE INVENTION

The present invention relates generally to medical devices, and particularly to repair of heart valves using annuloplasty rings.

BACKGROUND OF THE INVENTION

In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid, and pulmonary, and are each mounted in an annulus comprising dense fibrous rings attached either directly or indirectly to the atrial and ventricular muscle fibers.

Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood through the valve when the valve is closed. Valve disease can be severely debilitating and even fatal if left untreated.

Valve disease involving the mitral valve often involves secondary mitral regurgitation (MR), a complication of end-stage cardiomyopathy which is the backflow of blood from the left ventricle (LV) to the left atrium (LA) resulting from imperfections in the mitral valve. When the mitral valve allows blood to flow backward into the left atrium, the left ventricle must pump progressively harder to circulate blood throughout the body, which in turn promotes congestive heart failure (CHF).

Various surgical techniques may be used to repair a diseased or damaged valve. One method for treating defective valves is through repair or reconstruction. One repair technique that has been shown to be effective in treating incompetence is annuloplasty, in which the effective size and/or shape of the valve annulus is modified by securing a repair segment, such as an annuloplasty ring, around the heart valve annulus. For example, the valve annulus may be contracted by attaching a prosthetic annuloplasty repair segment or ring to an interior wall of the heart around the valve annulus. The annuloplasty ring is designed to support the functional changes that occur during the cardiac cycle: maintaining coaptation and valve integrity to prevent reverse flow while permitting good hemodynamics during forward flow.

The annuloplasty ring typically comprises an inner substrate, often formed from a metal (such as stainless steel or titanium) or from a flexible material (such as silicone rubber or Dacron cordage), which is typically covered with a biocompatible fabric or cloth to allow the ring to be sutured to the heart tissue. Depending on a particular application, annuloplasty rings may be stiff or flexible, may be split or continuous, and may have a variety of shapes, including circular, D-shaped, C-shaped, saddle-shaped, and/or kidney-shaped. Examples are seen in U.S. Pat. Nos. 5,041,130, 5,104,407, 5,201,880, 5,258,021, 5,607,471, 6,187,040, and 6,805,710, the contents of which are incorporated herein by reference in their entirety. Many annuloplasty rings are formed in a plane, but some rings are generally non-planar. Such non-planar rings can be saddle-shaped, and/or bowed along various portions, such as being bowed along their anterior or straight side to conform to the desired shape of the annulus at that location.

Implanting of annuloplasty rings can be a difficult procedure. Currently-available methods include open-heart surgery and so-called minimally-invasive procedures. One particular difficulty is firmly holding the ring during the surgery. It is possible to implant rings by clamping the ring with forceps and/or the surgeon's fingers, but in many circumstances a specifically tailored annuloplasty ring holder is desirable. Examples of annuloplasty ring holders are depicted in U.S. Pat. Nos. 5,350,420; 5,683,402; and 6,749,630, the contents of which are incorporated herein by reference in their entirety.

Using a standard atriotomy approach to the mitral valve for repair, the surgeon does not generally achieve straight-on access to the mitral valve annulus. Instead, the surgeon often sees and accesses the valve from an angle. Therefore, when the sutures are placed in the annuloplasty ring and it is "parachuted" down to the annulus, the ring and holder must be reoriented to sit flat against the annulus. In minimally-invasive (MIS) approaches to the mitral valve, the annuloplasty ring must be passed through a relatively small port into the chest. This can be complicated by the bulk of some holders, so in some instances a surgeon simply removes the holder from the ring prior to "parachuting" the ring down the sutures and onto the valve annulus. However, the removal of the entire holder from the ring can make control of the annuloplasty ring more difficult.

Another issue is visibility of the ring and valve annulus during the implantation procedure. Some holders block significant portions of the surgeon's view, which can make the surgical procedure more difficult. To enhance visibility, some holders make use of transparent and/or translucent materials. Some holders use a so-called "window" approach, wherein openings are positioned in the template portion of the holder. The openings serve as windows in the holder template through which the user can view the surgical procedure. Examples of such holders are described in U.S. Pat. Nos. 5,683,402 and 6,749,630, the contents of which are incorporated by reference herein in their entirety.

Another issue is securing the ring to the holder in a releasable but secure manner. Many holders use multiple retaining sutures to secure a ring to the holder. In order to release the ring from the holder, the user severs the retaining sutures. Increasing the number of sutures can cause the ring to be more securely held to the holder, but can increase the steps necessary for the surgeon to release the ring from the holder. Additionally, the positioning of the retaining sutures is important in that the user must be able to access and sever the sutures to release the ring from the holder. Many prior ring holders made use of suture wells located at various positions about the holder, with the location of such wells corresponding to locations about the ring including the posterior and anterior portions of the ring. During implantation procedures, some of these locations may be difficult for a surgeon to access in order to sever the suture.

Accordingly, there has been a need for an improved apparatus, system, and method to implant an annuloplasty ring. The present invention satisfies one or more of these needs.

SUMMARY OF THE INVENTION

The present application is generally described with respect to its use in the repair of the mitral valve, which regulates blood flow from the left atrium (LA) to the left ventricle (LV). However, the invention could also be applied to repair of other valves, such as the tricuspid or aortic valves.

The invention includes several features for annuloplasty ring holder technology. One feature is the application of reduced structural elements on the holder, including radial arms and other structures, to increase the visibility for the user during the implantation procedure. In addition to reducing the structural elements, placing the structural elements of the holder (including the post) toward the outer regions of the holder, which in turn places those elements toward the outer regions of the central opening bounded by the annuloplasty ring when the ring is attached to the holder, also provides enhanced visibility and accessibility of the ring as well as of the heart valve and other physiological structures underneath the ring.

In one embodiment of the invention, the holder includes a lower template forming a generally T-shaped configuration, with a radial arm forming the post of the T and a base template section, with two wing-like portions, forming the top bar of the T. The base template section is placed against a first portion of the ring, which may be an anterior portion configured for placement on the valve annulus adjacent an anterior leaflet. The base template section extends only partially into the area bounded by the ring, and preferably extends only approximately to or short of the geometric center of the bounded area. The handle post can be secured to the base template section so that the handle post is well away from the geometric center of the ring bounded area. The radial arm extends from the base template section across the ring bounded area to an opposing portion of the ring. If the base template section is placed against an anterior portion of the ring, the radial arm may extend from the base template section to a central or other section of the posterior portion of the ring.

A holder and ring combination according to an embodiment of the invention includes a generally triangular-shaped ring, with the ring having three segments joined adjacent their ends to form the generally triangular shape. The holder has a first base portion that runs generally parallel to one of the three segments. The holder has a radial arm that extends from the base portion to engage a junction between the other two segments. These other two segments are thus unsupported and uncovered by the holder for substantially their entire lengths except for their end portions.

Another feature is the use of an angled handle post, which is either fixed or adjustable. The angled handle post may also be rotationally adjustable about the longitudinal axis of the holder. Angling the handle post with respect to the plane of the annulus permits the user greater visibility during an implantation procedure.

Another feature is the improved placement of suture wells, and improved suturing techniques that facilitate severing the suture lines and assembly of the device. In one embodiment the suture wells are placed toward the outer regions of the holder, away from the handle post, so that the user can more easily access the suture wells to cut the retaining suture lines.

Other features and advantages of the present invention will become apparent from the following detailed description, taken in conjunction with the accompanying drawings which illustrate, by way of example, the principles of the invention.

BRIEF DESCRIPTION OF THE DRAWINGS

FIGS. 1A and 1B depict perspective views of an assembly having a ring holder and handle according to an embodiment of the invention;

FIGS. 2A-2C are various views of the annuloplasty ring from FIG. 1;

FIGS. 3A-3F are various views of the ring holder from FIG. 1;

FIG. 4 is a top view of a ring holder according to an embodiment of the invention;

FIG. 5 is a top view of a ring holder according to an embodiment of the invention;

FIG. 7 is a perspective view of a portion of a ring holder according to an embodiment of the invention;

FIG. 8 is a perspective view of a portion of a ring holder according to an embodiment of the invention;

FIG. 9 is an exploded perspective view of the portion of the ring holder depicted in FIG. 8;

FIGS. 13A through 13H are perspective, back, top, bottom, front, front in cross section, side, and side in cross section views, respectively, of the annuloplasty ring holder from FIGS. 12A and 12B;

FIGS. 14A through 14E are top, bottom, front elevational, rear elevational, and side elevational views, respectively, of the annuloplasty ring from FIGS. 12A and 12B; and FIGS. 15A-15E are various perspective views of an annuloplasty ring and holder from FIGS. 12A and 12B being used to implant a ring in a patient.

DETAILED DESCRIPTION OF THE INVENTION

Figure 1:
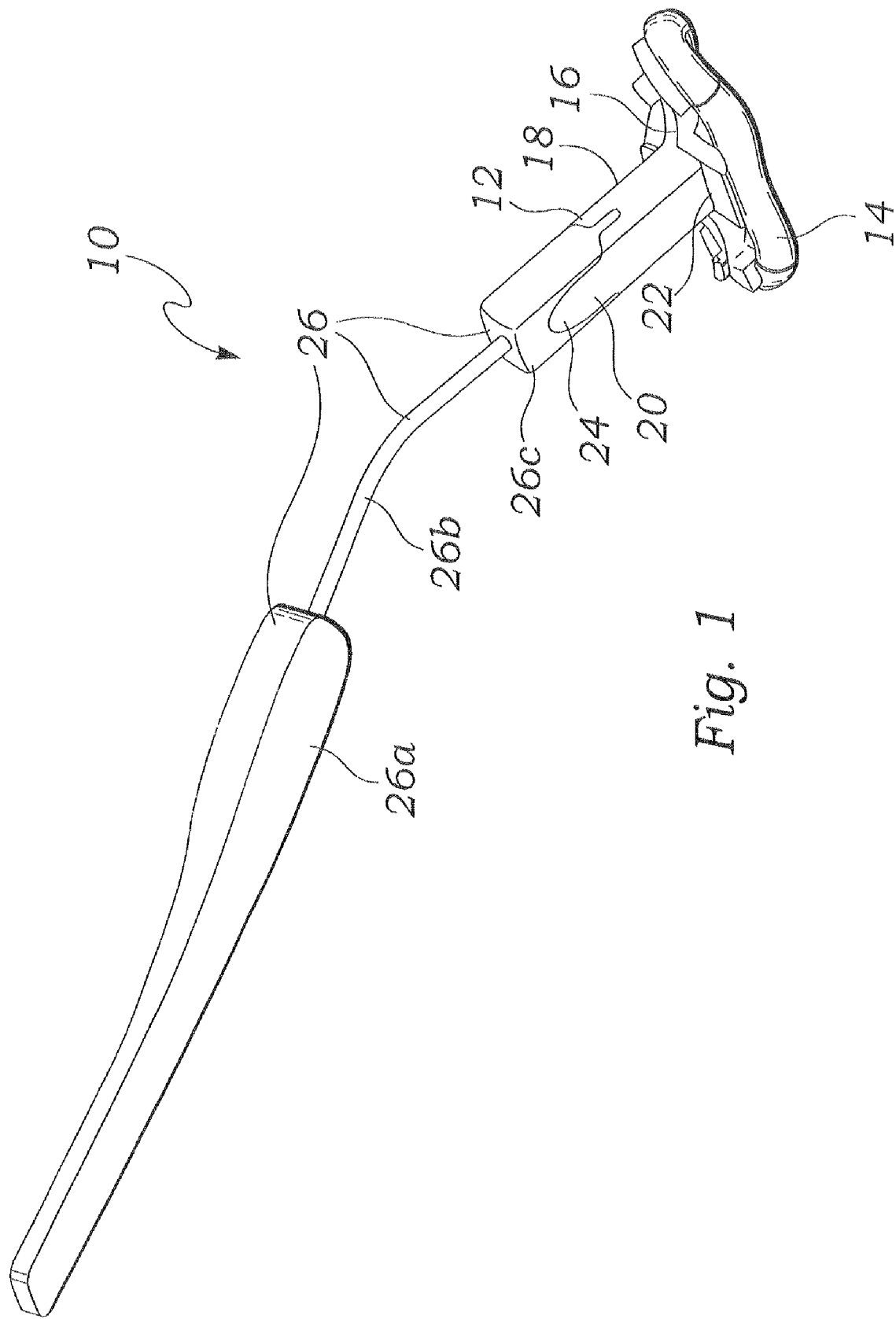
FIG. 1 depicts a perspective view of an assembly having a ring, ring holder, and handle according to an embodiment of the invention.
Figure 3F:
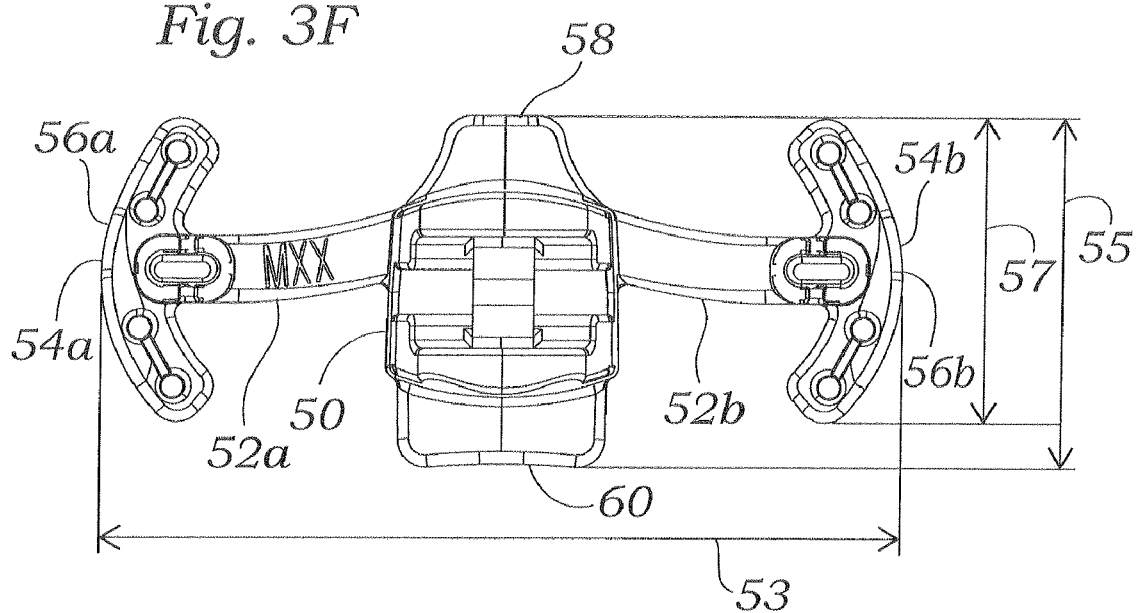
Figure 3E:
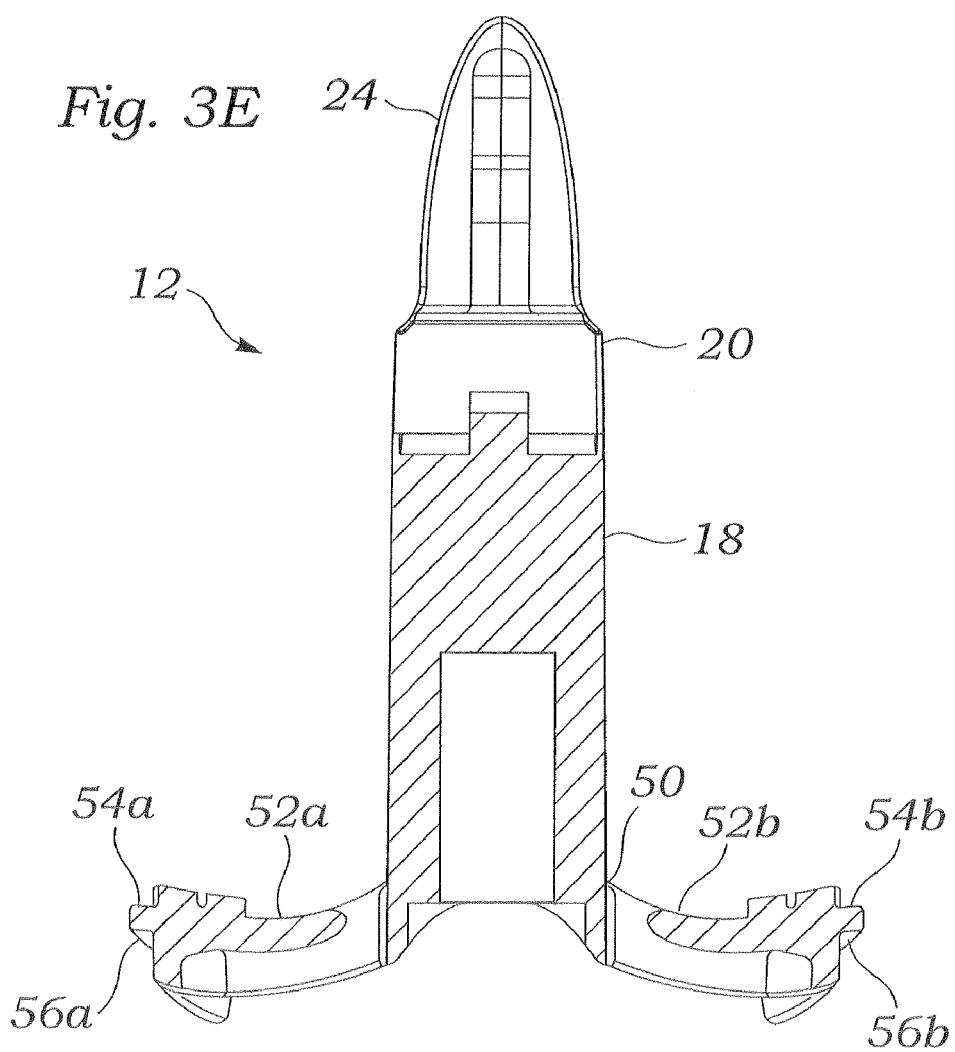

One embodiment of the invention is depicted in FIG. 1. The device 10 comprises a holder 12 and annuloplasty ring 14. The holder 12 has a lower template portion 16 secured to a handle post 18. In the embodiment depicted, the handle post 18 has a proximal end 20 and distal end 22, with the distal end 22 secured to the template portion 16. The handle post proximal end 20 includes an attachment assembly 24 by which a handle 26 can be removably secured to the handle post 18. The handle 26 includes a proximal portion 26a, a middle portion 26b, and a distal (attachment) portion 26c. The distal portion 26c is configured to cooperate with the attachment assembly 24 in order to secure the handle 26 to the handle post 18. The middle portion 26b of the handle may be malleable, thereby permitting a surgeon to adjust (via bending) the handle to a configuration convenient for the particular application and surgeon.

Attachment and removal of the handle 26 to and from the handle post 18 are depicted in FIGS. 1A and 1C. The handle 26 can be secured to the handle post 18 by snapping the handle distal portion 26c into the attachment assembly 24. Removing the handle 26 is accomplished by gripping the holder 12 while pulling the handle 26.

FIGS. 2A-2C are plan, front elevational, and side elevational views, respectively, of an annuloplasty ring 14 from FIG. 1. The ring 14 is generally oval-shaped about a major axis 30 and a minor axis 32 with a maximum height dimension 33 measured parallel to the minor axis 32. The ring has a posterior portion 34, an anterior portion 36, and sides 38, 40. A mid-section 42 of the posterior portion 34 of the ring 14 bows upward and inward. The elevation 43 above a datum plane 44 is seen in FIG. 2B, while the magnitude of the inward bow of the mid-section 42 is seen in FIG. 2A. The sides 38, 40 also bow upward as indicated in FIG. 2B. Finally, the anterior portion 36 bows upward and inward. The mid-section 42 forms a plateau 46 in the Z-direction centered about the minor axis 32 as seen in FIG. 2B. The ring can be formed from various materials, such as stainless steel, titanium, Stellite, cloth, etc. The choice of materials and specific design of the ring depend on the particular application. In the embodiment of FIGS. 2A-2C, the ring 14 has a specific shape. However, other shapes are also within the scope of the invention. The ring may be relatively flexible or relatively stiff, or may be a combination of stiff and flexible portions.

FIGS. 3A-3F depict the holder 12 from FIG. 1 in greater detail. The holder 12 includes a central base portion 50. First and second arms 52a, 52b extend from the central base portion 50. At the distal ends 54a, 54b of the first and second arms 52a, 52b are ring securing portions 56a, 56b against which one or more portions of an annuloplasty ring can be positioned. The holder 12 has a maximum width 53 and a maximum height 55. In the embodiment depicted, the securing portions 56a, 56b include generally arcuate segments which are configured to engage side portions 38, 40 of the annuloplasty ring depicted in FIGS. 2A-2C. In the embodiment of FIGS. 3A-3F, the generally arcuate segments are relatively short, having a height 57 less than the maximum height 55 of the holder 12.

In the embodiment of FIGS. 3A-3F, a posterior knob portion 58 is configured to engage a posterior portion 34 of the annuloplasty ring 14, and an anterior knob portion 60 is configured to engage an anterior portion 36 of the annuloplasty ring 14. The knob portions 58, 60 provide additional support to the annuloplasty ring 14. Although the embodiment depicted in FIGS. 3A-3F has knob portions 58, 60 that lack any suture holes through which sutures can pass to secure the ring to the knob portions, such sutures and knob portion suture holes are within the scope of the invention.

The holder 18 can be formed from various materials, or combinations of different materials, depending on the particular application. In one embodiment, the holder 12 is formed from a clear polysulfone. The holder 12 may also include markers for visibility under surgical conditions, such as radiopaque markers. In the embodiment depicted in FIG. 3D, the holder 12 includes a radiopaque marker 51 imbedded within the handle post 18. Such a radiopaque marker can be formed of various materials, such as polyphenylsulfone with 14% radiopaque bismuth subcarbonate.

In the embodiment depicted in FIGS. 3A-3F, the only structure leading from the central base portion 50 out to the annuloplasty ring is the two arms 52a, 52b and the knob portions 58, 60. By limiting the size (when viewed by the user from above) of the structure within the area enclosed by the ring (i.e., the central base portion 50, the arms 52a, 52b, and the knob portions 58, 60), the visibility afforded the user during the surgical procedure is improved over products having greater mass within the area enclosed by the ring.

Depending on the particular application, including the type of ring being delivered and whether the ring rigid or flexible, one or both of the knobs 58, 60 and/or one or both of the arms 52a, 52b may be eliminated to further enhance the visibility. For example, in the embodiment depicted in FIG. 4, the knobs have been eliminated in favor of the arms 52a, 52b. The central base portion 50 has a maximum height 59 and maximum width 61. In the embodiment of FIG. 5, the arms have been eliminated in favor of the knobs 58, 60. The knobs 58, 60 each have suture holes 62 and corresponding cutting wells 64 through which sutures may pass to secure the ring to the knobs and holder. The knobs 58, 60 narrow toward their distal ends to distal widths 63, 65.

The central base portion 50 may also be further reduced in size, as may the knobs 58, 60 and arms 52a, 52b. The arms and/or knobs may also be relocated to different locations on the central base portion 50, depending on the particular application.

Figure 6:
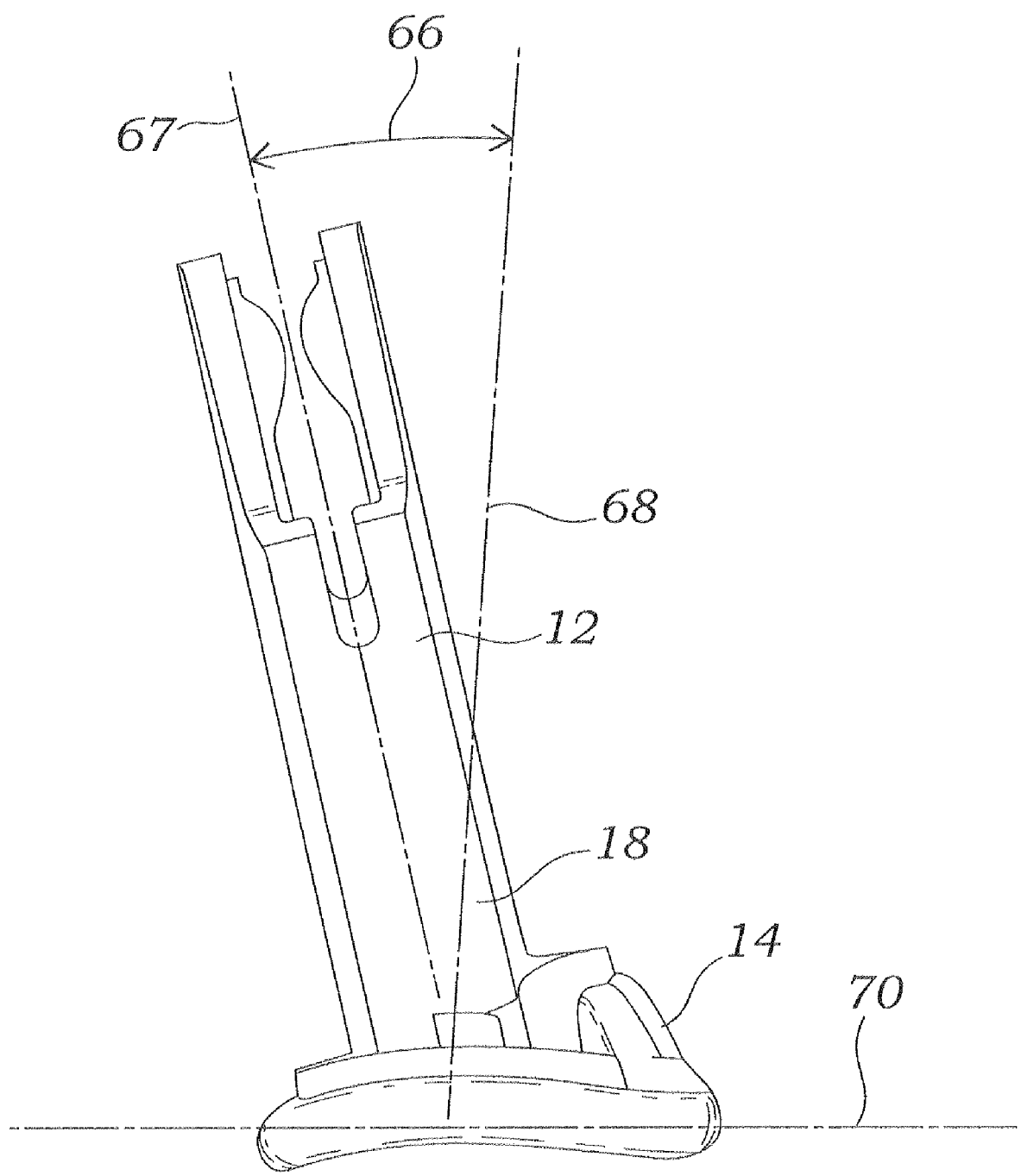
FIG. 6 is a side view of a ring holder according to an embodiment of the invention.

Another aspect of the invention is the positioning of the handle post with respect to the ring. By applying an appropriate angle to the handle post of the holder with respect to the ring, the plane of the ring will naturally be parallel to the plane of the annulus. This allows for more intuitive orientation of the ring, and parachuting of the ring down to the annulus without reorientation. In the embodiment depicted in FIG. 6, the longitudinal axis 65 of the handle post 18 is positioned at an angle 66 from a vertical plane 68 normal to the datum plane 70 of the ring 14. In the particular embodiment depicted, the angle is approximately 11 degrees, although other angles are also within the scope of the invention. For example, angles between 10 and 15 degrees may be useful for ring holders. Other angles can also be selected, depending on the particular application.

The optimal angle may not be constant for every patient or surgeon. For example, different patients often have different physical characteristics of their respective mitral valves. Also, different surgeons may use slightly different approaches to the mitral valve, or may have certain preferences with respect to viewing angles, etc.

A single-pivot structure can be helpful in adjusting the angle as desired. As depicted in FIG. 7, a handle post 18 having a proximal portion 18a and a distal portion 18b, with the distal portion 18b secured to the central base portion (not shown) of the holder 12. The proximal portion 18a can be pivoted with respect to the distal portion 18b, which permits a user to adjust the handle post angle to achieve the optimal angle for the specific application. The proximal portion 18a has a toothed fitting 72a configured to interlock with a corresponding toothed fitting 72b on the distal portion 18b. Each toothed fitting has a corresponding pin hole 74a, 74b at its center. A releasable compression pin 76 is configured to pass through the pin holes 74a, 74b. With the compression pin 76 tightened in place, it holds the toothed portions 72a, 72b in engagement, maintaining a fixed angle between the proximal portion 18a and distal portion 18b of the handle post 18. With the compression pin 76 loosened, the user can adjust the angle between the proximal portion 18a and distal portion 18b of the handle post 18, and then lock the pin 76 into its tightened configuration in order to fix the proximal portion 18a and distal portion 18b at the desired angle.

In another embodiment of the invention, the holder may include the ability to change not just the holder angle but also the rotational position of part of the holder with respect to the central base portion. In the embodiment of FIGS. 8 and 9, the handle post 18 includes a distal portion 18b fixed to the central base portion 50. A handle post proximal portion 18a is rotationally secured to the distal portion, so that the proximal portion 18a can rotate about the holder longitudinal axis 78. The rotation of the proximal portion 18a can be controlled by conventional methods, such as having a releasable lock (not shown) that selectively prevents rotation.

To permit adjustment of the angle between the ring datum plane and a portion of the post, the handle post 18 has an additional proximal structure 80 that can be adjusted in angle 81 with respect to the ring datum plane and holder longitudinal axis 78. The additional proximal structure 80 can be releasably and/or adjustably secured to the rest of the handle post 18 so that the angle 81 can be modified as the user desires. Conventional structures can be used to accomplish this feature.

In the embodiment of FIGS. 8-9, a rotational ball and retainer structure is used. The additional proximal structure 80 includes a ball 82 configured to cooperate with a corresponding recess 84 in the handle post distal portion 18b. An adjustable housing 85, which also forms the handle post proximal portion 18a, is configured to hold the ball 82 against the recess 84. The adjustable housing 85 includes a slit 90, which facilitates removal of the adjustable housing from the additional proximal structure 80 and also permits the additional proximal structure 80 to be rotated to relatively extreme angles. The adjustable housing 85 can be screwed onto the handle post distal portion 18b via corresponding threading 86, 88 on the handle post distal portion 18b and in the adjustable housing 85. By loosening (i.e., unscrewing) the adjustable housing 85 from the handle post distal portion 18b, a user will loosen the additional proximal structure 80 and permit adjustment of the angle and rotation thereof. Once the desired angle and rotation are achieved, the user can tighten the adjustable housing 85 onto the handle post distal portion 18b, which will secure the additional proximal structure 18 at the desired angle and rotation.

Another embodiment involves a similar ball and housing structure to that depicted in FIGS. 8 and 9, but with the ball structure positioned on the handle post and the adjustable housing on the additional proximal structure. In this embodiment, the ball is attached to the holder and the housing is lengthened and turned upside down to become part of the handle and/or additional proximal structure. There is an additional structure that threads inside of the housing. At the distal end of this structure there is mechanism that allows a user to thread the structure into or out of the housing and thus move the structure relative to the housing. At the other end of the structure there is a recess that conforms to the shape of the ball. With this embodiment, a user can tighten or loosen the housing by rotating the handle and/or additional proximal structure. This permits a surgeon to make an adjustment to angle and rotation at a distance (i.e. by turning a knob at the end of the handle).

In minimally invasive surgery (MIS) approaches to the mitral valve, the annuloplasty ring must be passed through a relatively small port into the chest. This can be complicated by some holders, which can interfere with introducing the annuloplasty ring into the chest. Depending on the particular application, the current invention's feature of adjusting the handle post angle and/or rotational position can also allow easier passage of the ring and holder into the chest cavity. Such adjustment can occur before and/or during the surgical procedure. For example, a surgeon may select an initial rotation and angle during initial surgical procedures, then select another rotation and/or angle for introduction of the ring and holder through the chest wall, and then select still another rotation and/or angle for final placement of the ring.

Figure 10A:
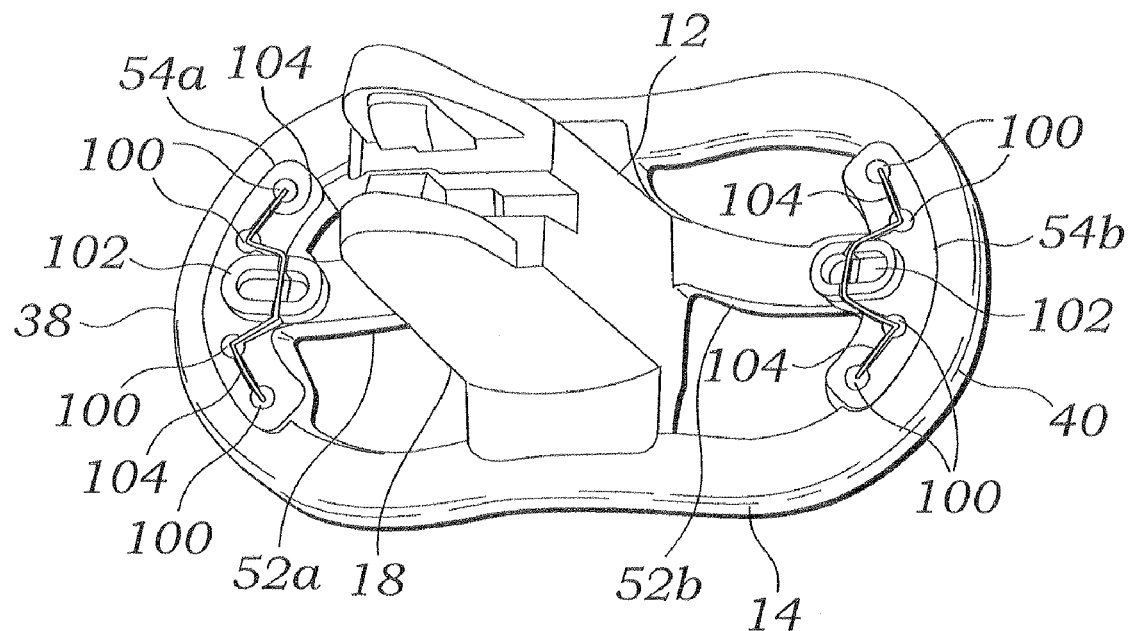
FIG. 10A is a perspective view of ring and ring holder according to an embodiment of the invention.

Another feature of the invention is depicted in FIG. 10A, which depicts a holder 12 and ring 14. Suture holes 100 are positioned at distal ends 54a, 54b of the arms 52a, 52b, with corresponding suture wells 102 positioned on the arms 52a, 52b. In the embodiment of FIG. 10, the suture wells 102 are positioned on the arms 52a, 52b to correspond with the sides 38, 40 of the ring 14. Restraining sutures 104 pass through the suture holes 100 and suture wells 102. The suture wells 102 are configured to provide an easily accessible location for the surgeon to cut the suture 104 passing therethrough. Due to the structure of the particular ring 14, which is relatively short along its minor axis when compared to its length along the major axis, the areas of the ring 14 and holder 12 corresponding to the ring sides 38, 40 are generally the areas which are most easily accessible to the surgeon during an implantation procedure. By positioning the suture wells 104 at these areas (which are furthest away from the holder central portion and post), the invention facilitates the ease by which the surgeon can sever the restraining sutures in order to release the ring 14 from the holder 12.

Figure 10B:
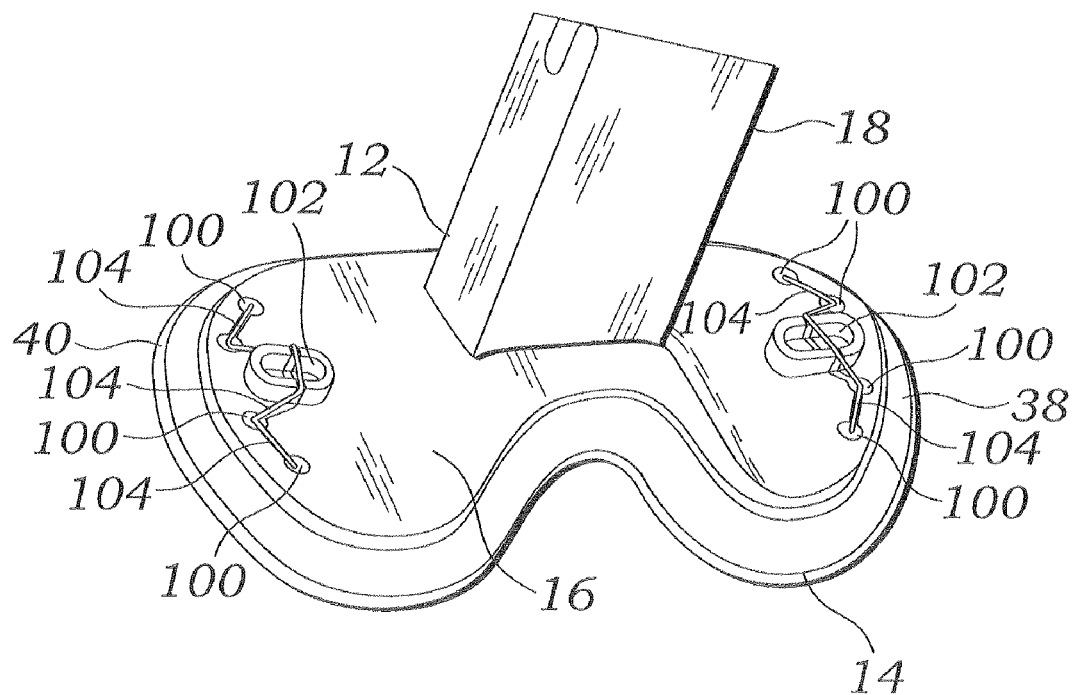
FIG. 10B is a perspective view of ring and ring holder according to an embodiment of the invention.

A similar embodiment is depicted in FIG. 10B, which has a holder 12 and ring 14. The holder 12 of FIG. 10B has a generally solid lower template portion 16 (instead of the arms 52a, 52b depicted in FIG. 10A). In the embodiment of FIG. 10B, the suture wells 102 are positioned on the lower template portion 16 to correspond with the sides 38, 40 of the ring 14. Restraining sutures 104 pass through the suture holes 100 and suture wells 102. The suture wells 102 are configured to provide an easily accessible location for the surgeon to cut the suture 104 passing therethrough.

In the embodiments depicted in FIGS. 10A and 10B, there are only two suture wells. However, other numbers of suture wells, from one (1) and up, are within the scope of the invention, depending on the particular number of sutures. As a general rule, fewer sutures and corresponding suture wells leads to greater ease in cutting the sutures. By limiting the number of sutures and/or suture wells, and by positioning the suture wells at those areas that are easiest to access, the invention facilitates the ease by which the surgeon can sever the restraining sutures.

Figure 11:
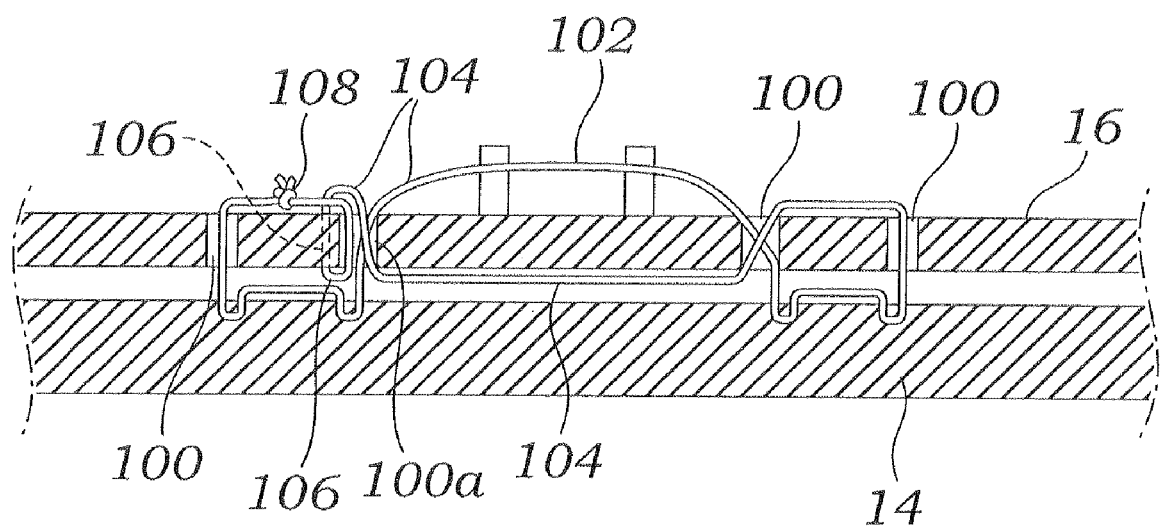
FIG. 11 is a side view, in cross-section, of a portion of a ring and ring holder according to an embodiment of the invention.

Another feature of the invention is an improved suture routing approach. The approach is depicted in FIG. 11, wherein a single piece of suture line 104 passes in the depicted pattern through the various suture holes 100, across the suture well 102, and through portions of the ring 14. For one suture hole 100a, the suture line 104 passes through the suture hole 100a, then is looped around a flange or other edge of the holder 14, and then passes back through the suture hole 100a (in the same direction that it passed through previously), thereby providing resistance to the suture slipping with respect to the holder 106. The suture 104 is tied to itself. In the embodiment depicted, a double square knot 108 is used to secure the suture 104 to itself. Note that other knots are also within the scope of the invention. The described suture routing provides wider attachment points for greater stability of the ring on the holder, without increasing the likelihood of a high suture pull-out resistance.

Figure 12A:
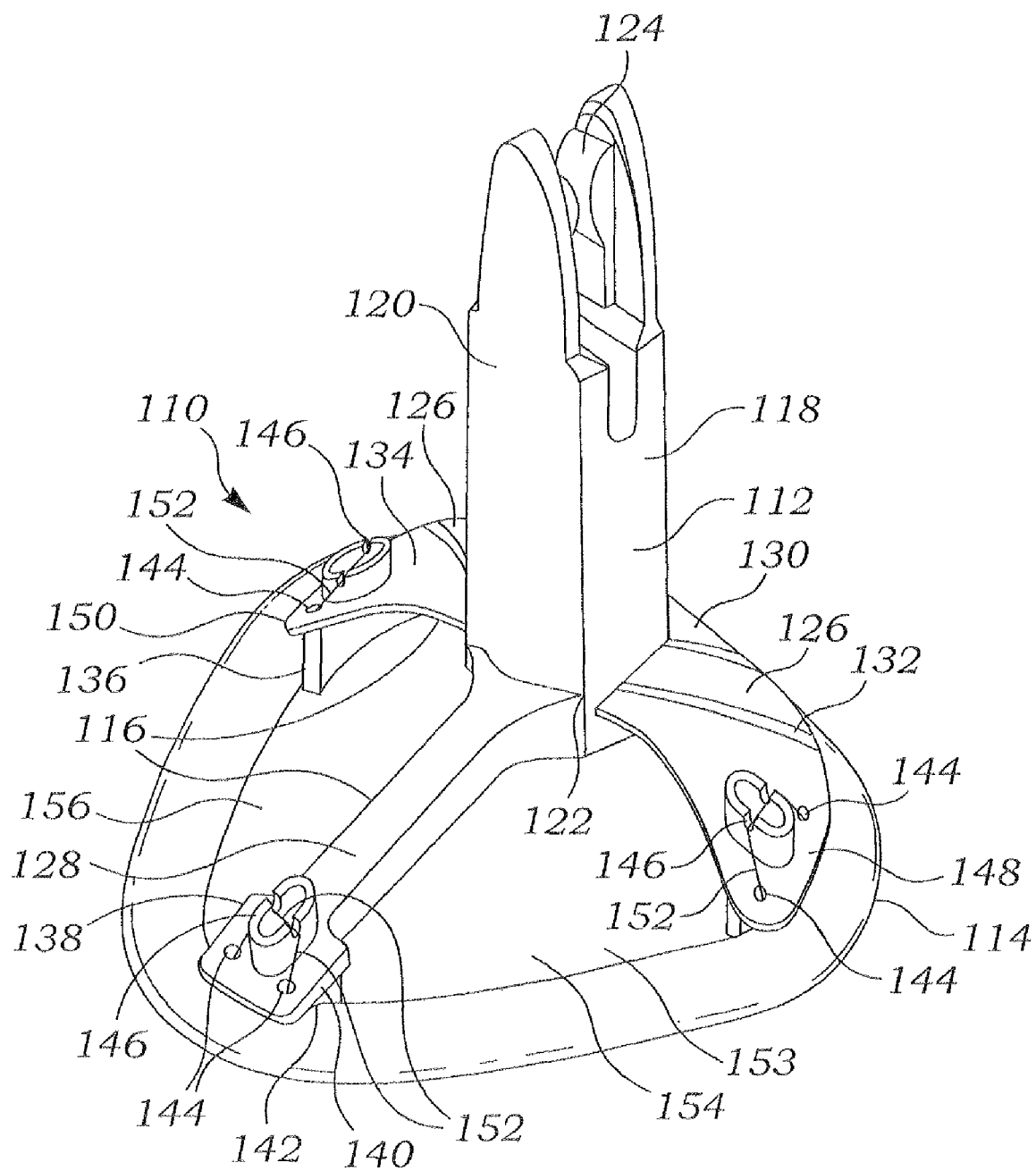
FIGS. 12A and 12B are perspective and top views, respectively, of a ring and ring holder according to an embodiment of the invention.

FIG. 12A depicts a further embodiment of the invention, wherein a ring delivery system 110 includes a holder 112 having an annuloplasty ring 114 secured thereto. The particular annuloplasty ring holder 112 is configured to fit the particular ring 114 depicted, which is itself sized and configured for placement on or in the mitral valve. However, other holder configurations and sizes are also within the scope of the invention, including holders configured to hold annuloplasty rings having different sizes and configurations, and holders for rings configured to placement in other valves, e.g., tricuspid valves, etc.

The holder 112, which is depicted in FIGS. 13A-13H without the ring 114, has a lower template portion 116 secured to a handle post 118. In the embodiment depicted, the handle post 118 has a proximal end 120 and distal end 122, with the handle post distal end 122 secured to the template portion 116. The handle post proximal end 120 includes an attachment assembly 124, similar to that depicted in the embodiment of FIGS. 1, 1A-1B, and 3A-3F, by which a handle can be removably secured to the handle post 118. The holder 112 can be used with a handle such as that depicted in FIGS. 1 and 1A-1C, or with other handles, depending on the particular application.

The holder 112 has a lower template portion 116 that is formed from two parts: a base template section 126 and a radial arm 128, which together form a generally "T"-shaped structure with the radial arm 128 forming the base of the T and the base template section 126 forming the cross bar of the T. The base template section 126 includes a middle portion 130 positioned adjacent the handle post distal end 122 and first and second wing portions 132, 134 extending from opposing sides of the handle post distal end 122. As seen in FIGS. 13A, 13B, 13E, and 13F, the first and second wing portions 132, 134 curve downward at their distal ends. The base template section 126 includes a notch 136 configured to abut against the ring 114, with the notch 136 forming a generally continuous path passing along the outer/lower areas of the middle portion 130 and wing portions 132, 134.

The radial arm 128 includes a radial arm distal end 138 with a ring securing portion 140 thereon. The ring securing portion 140 includes a small notch 142 which is configured to engage against the ring 114, similar to the longer notch 136 of the base template section 126.

The holder 112 includes suture holes 144 adjacent to corresponding suture wells 146, positioned at the distal portion of the radial arm 128 and the distal portions 148, 150 of the template wing portions 132, 134. As depicted in FIG. 12A, restraining sutures 152 pass through the suture holes 144 and suture wells 146. The suture wells 146 are configured to provide an easily accessible location for the surgeon to cut the suture 152 passing therethrough. Due to the structure of the particular ring 114, the areas of the ring 114 and holder 112 corresponding to the template wing portion distal ends 148, 150, as well as the radial arm distal end 138, are generally the areas which are most easily accessible to the surgeon during an implantation procedure. By positioning the suture wells 146 at these areas (which are furthest away from the holder central portion and post), the invention facilitates the ease by which the surgeon can sever the restraining sutures 152 in order to release the ring 114 from the holder 112.

In the embodiments depicted in FIGS. 12A-12B and 13A-13H, there are three suture wells 146. However, other numbers of suture wells, from one (1) and up, are within the scope of the invention, depending on the particular number of sutures, the shape and size of the ring, etc. As a general rule, fewer sutures and corresponding suture wells leads to greater ease in cutting the sutures. By limiting the number of sutures and/or suture wells, and by positioning the suture wells at those areas that are easiest to access, the invention facilitates the ease by which the surgeon can sever the restraining sutures.

Figure 12B:
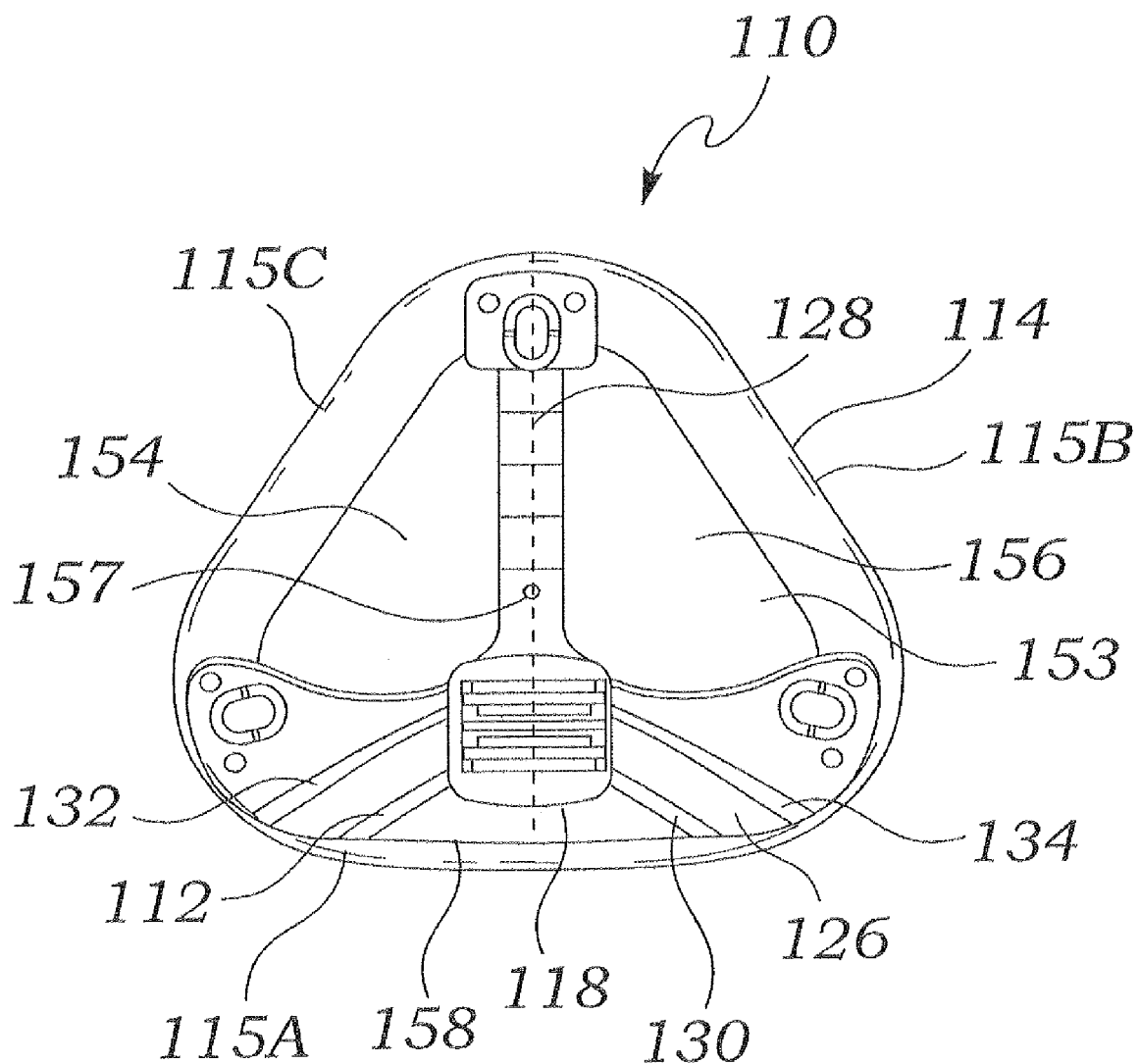

The combination of features of the holder 112 and ring 114 together provide an improved ring delivery system. As seen in FIG. 12B, the particular ring 114 is generally in the shape of an isosceles triangle, with the ring 114 having three generally straight segments 115a, 115b, 115c that are connected toward their ends to form the triangular shape. One of the generally straight segments 115a forms an anterior portion of the ring 114, while the remaining generally straight segments 115b, 115c form a posterior portion of the ring 114. The base portion 126 is generally straight and elongated, and with its wings 132, 134 runs generally parallel with one of the generally straight segments 115a. In the particular embodiment depicted, the (anterior) generally straight segment 115a is adjacent to and supported by the holder 114 for essentially the entire length of the generally straight segment 115a. The radial arm 128 extends to engage a junction between the other generally straight segments 115b, 115c. These other generally straight segments 115b, 115c are thus left generally free of the holder 114 along their lengths except for their end portions. The suture wells 146 of the holder 112 are positioned adjacent the end portions of the generally straight segments 115a, 115b, 115c, which correspond to the corners of the generally triangular shape of the particular ring 114 depicted.

Figure 13E:
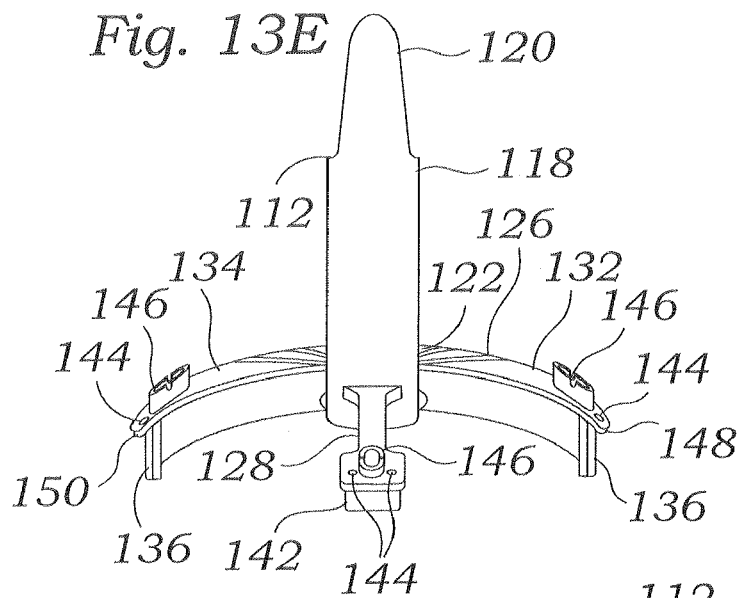
Figure 13F:
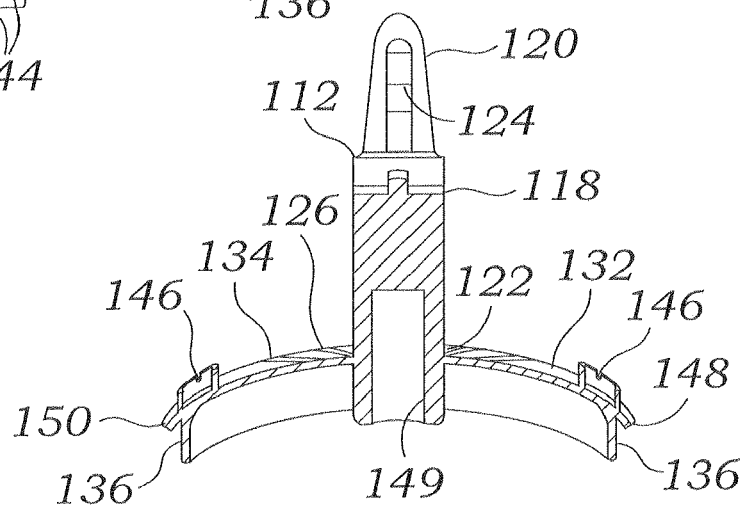
Figure 13G:
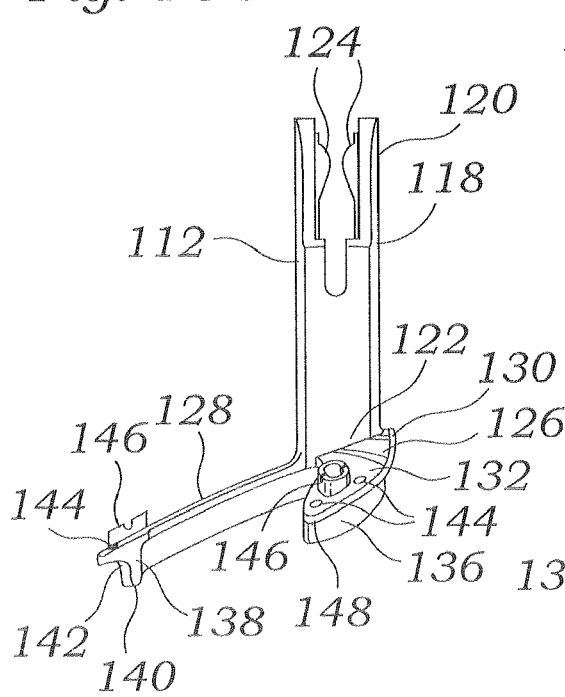
Figure 13H:
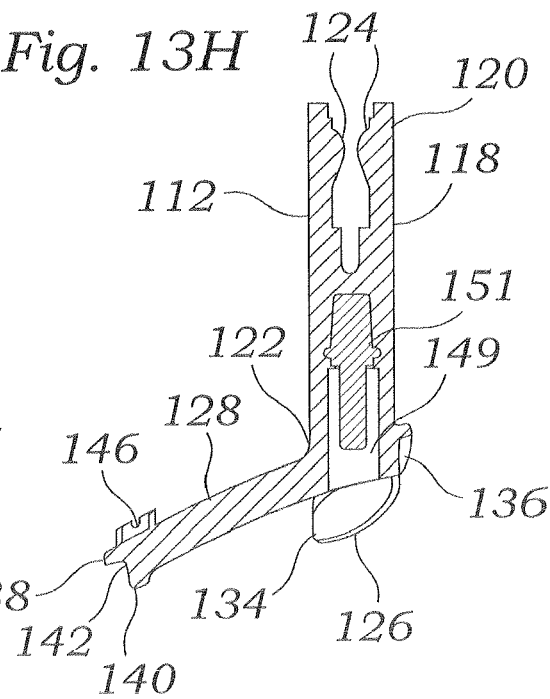

In the particular holder embodiment depicted in the cross-sectional views of FIGS. 13F and 13H, the holder 112 includes a hollow opening 149 passing through the lower template portion 116 and into the lower portion of the handle post 118. As depicted in FIG. 13H, the holder 112 may include a radiopaque marker 151 or other visualization reference that can enhance the visibility of the holder 112 under fluoroscopy or other visualization methods. In the particular embodiment of FIG. 13H, the radiopaque marker 151 extends from within the handle post 118 and into the hollow opening 149.

FIG. 12B is a top view of the system 110, viewed from a position similar to that a surgeon or other user will encounter during an annuloplasty ring installation procedure. The combination of relatively a relatively narrow base template section 126 (which in the particular embodiment depicted comprises two narrow wing portions 132, 134) and the generally thin radial arm 128, provides enhanced viewing through the system 110 via large open areas 154, 156 within the area 153 bounded by the ring 114. In the particular embodiment depicted, the relatively narrow base template section 126 is positioned adjacent the ring 114 along an outer portion of the bounded area 153, and does not extend into the bounded area 153 far enough to extend over the ring geometric center 157. The radial arm 128 does extend over the geometric center 157, but is sufficiently narrow that visibility is still maintained through most of the bounded area 153. By positioning the handle post 118 adjacent an outer edge of the holder 112 and away from the geometric center 157 of the area 168 bounded by the ring 114, and more specifically (in the particular embodiment depicted) adjacent the outer edge 158 of the middle section of the middle portion 130 of the base template section 126, the handle post 118 and any handle that might be attached thereto are positioned generally out of the way, thereby providing enhanced viewing of and access to the surgical site by the surgeon or other user.

The invention can include annuloplasty rings of various construction and configuration. In one preferred embodiment, an annuloplasty ring of the present invention comprises a continuous ring body which may be made of metal, such as a titanium alloy, or other appropriate material. A tubular sleeve or outer band, which may be formed from silicone, is around the ring body. Finally, a tubular fabric covering around the silicone sleeve provides an anchoring platform for sutures or other attachment devices such as staples. The fabric covering is typically Dacron (polyethylene terephthalate). The tubular fabric covering around the silicone sleeve provides an interface for securing the annuloplasty ring to the mitral annulus, although other interfaces are contemplated. For example, rings having outward hooks or barbs are known in the art.

FIGS. 14A through 14E depict the ring 114 from FIGS. 12A and 12B, separate from the holder, in greater detail. Similar rings are disclosed in U.S. patent Publication No. 2008/0058924, entitled "Saddle-Shaped Annuloplasty Ring" and filed concurrently herewith, the contents of which are expressly incorporated by reference herein. Other rings that could be used with the system and holder of the invention are disclosed in pending U.S. Pat. No. 7,294,148, entitled "Annuloplasty Ring for Mitral Valve Prolapse" and filed on Apr. 29, 2004; and in U.S. Patent Publication No. 2006-0129236, entitled "Annuloplasty Ring for Mitral Valve Prolapse" and filed on Feb. 2, 2006, the contents of each of which are hereby incorporated by reference in their entirety.

FIGS. 14A-14E illustrate the completed ring 114 so that a fabric covering is all that is visible. The annuloplasty ring 114 is depicted in the top view of FIG. 14A with a modified oval shape (closed) surrounding a central opening 153. The ring 114 is oriented about a central flow axis 170. The flow axis 170 defines an upward direction and a downward direction, corresponding to the top and bottom of the page relative to the ring 114 as seen in FIGS. 14C-14E. The downward direction corresponds to the direction of blood flow through the mitral valve annulus from the left atrium to the left ventricle, such that down is synonymous with the inflow direction and up is synonymous with the outflow or regurgitative direction of the valve. Looking along the flow axis 170 in FIG. 14A, the ring 114 has a major axis 172 perpendicular to a minor axis 174, the major and minor axes 172, 174 being perpendicular to the flow axis 170. It should also be understood that the "flow axis" here may not necessarily be the center of the volumetric flow through the annulus, but is instead orthogonal to the major and minor axes 172, 174, and therefore defines the gross direction of flow. The ring 114 also has a geometric center 157 in plan view, which is defined as the geometric center of the ring bounded area 153. Depending on the geometry of a particular ring, a flow axis may or may not align with a geometric center. In the particular embodiment of FIG. 14A, the flow axis 170 is positioned some distance from the geometric center 157.

A major axis dimension 176 is shown extending horizontally across the interior of the ring 114 the plan view of FIG. 14A. Likewise, a major axis dimension 178 is shown extending across the interior of the ring 114. In one preferred embodiment, the ratio of the minor axis dimension 178 to the major axis dimension 176 is about 3.5:4 (87.5%). Other ratios are also within the scope of the invention.

A bottom view of the ring 114 is depicted in FIG. 14B. The bottom of the ring 114 includes a marker in the form of a colored thread 179 to indicate that this side of the ring 114 is intended to lie against the valve annulus when implanted.

For purpose of further definition, a pair of trigone markers T1 and T2 is shown on the ring 114 corresponding to the approximate location of the fibrous trigones of the mitral annulus when the ring 114 is implanted. An anterior segment 180 extends around an anterior portion of the ring 114 between the trigone markers T1, T2. When the ring 114 is implanted, the anterior segment 180 will coincide with the anterior aspect of the mitral valve annulus. The anterior segment 180 is shown generally straight in the midsection when viewed from the top in FIG. 14A or bottom in FIG. 14B, but has an upward bow that can be seen in the anterior end view of FIG. 14D. Other shapes of the anterior segment are also within the scope of the invention, including curved or bowed portions to better conform to the anterior aspect of the native annulus.

The remainder of the ring 114 aside from the anterior segment 180 between the trigone markers T1, T2 will be termed the posterior portion 182, and is shown broken up into three sequential segments denoted P1, P2, and P3 (in series counter-clockwise from the first trigone marker T1), with the dividing line between P1 and P2 indicated as P12, and the dividing line between P2 and P3 indicated as P23. The precise angular dividing line between these three segments P1, P2, P3 is not standardized, though they are intended to generally correspond to the three visible cusps of the posterior leaflet of the mitral valve. In an exemplary embodiment, the three segments P1, P2, P3 are approximately equal in angular dimension, and the middle segment P2 is symmetric about the minor axis 174. It should be noted that annuloplasty rings are shaped and marked so as to be orientation-specific, such that the anterior segment is adapted to be implanted against the anterior aspect of the mitral annulus, and the same with the posterior portion.

The annuloplasty ring 114 has a modified D- or oval shape in plan view because of an outward bow 184 within the middle segment P2 of the posterior portion of the ring. Stated another way, the middle segment P2 of the posterior portion 182 of the ring 114 has an outward curve (convexity) more pronounced than adjacent sections (which may also be convex or relatively straight). The outward bow 184 thus bulges outward from the adjacent sections as compared to a conventional 3:4 ratio "D-shaped" annuloplasty ring such as the relaxed shape of a Carpentier-Edwards Physio® annuloplasty ring available from Edwards Lifesciences of Irvine, Calif. (www.edwards.com). In the particular embodiment depicted, the ring 114 includes a posterior portion central marker 185 designating the center point of the posterior portion 182.

As mentioned above, the outward bow 184 preferably results in a minor-major axis dimensional ratio of 3.5:4 (87.5%), although the present invention encompasses other rings, including in another preferred embodiment rings having an outward bow 184 that produces ratios of between about 3.3:4 (82.5%) and 4:4 (100%).

It is important to note that although the minor axis dimension 178 may increase relative to conventional D-shaped rings, the major axis dimension 176 can remain substantially the same. Furthermore, although the outward bow 184 is shown within the middle segment P2 of the posterior portion 182 of the ring, the entire section of the posterior portion that is posterior of the major axis 172 may be affected. That is, the outward bow 184 may extend into one or both of the first and third segments P1 and P3 of the posterior portion 182. In a preferred embodiment, however, the annuloplasty ring 114 only diverges from a conventional oval- or D-shaped ring (such as the Carpentier-Edwards Physio® ring) within the middle segment P2. In an exemplary embodiment, the angular extent of the outward bow 184 as measured about the central axis 170 is between 90-130 degrees, and more preferably about 128 degrees.

In conjunction with the outward bow 184, the posterior portion 182 of the annuloplasty ring 114 also includes a posterior upward bow 186 seen in FIG. 14C. The term "upward bow" refers to either an upward divergence from a planar ring, or an upward divergence from a so-called "saddle-shaped" ring. Therefore, the present invention encompasses both planar and saddle-shaped rings having an outward and upward posterior bow.

A height 188 of the posterior upward bow 186 is indicated in FIG. 14C and desirably exceeds about 3 mm, preferably more than about 4 mm, and most preferably between about 3-10 mm. The posterior upward bow 186 may or may not be formed in the ring 114 around the same angular extent as the outward bow 184. In a preferred embodiment, the outward bow 184 spans a smaller angular extent than the posterior upward bow 186, although they may start and end at the same location around the ring 114. Likewise, both the outward bow 184 and posterior upward bow 186 are desirably centered along the minor axis 174, although one or both may be asymmetrically offset. It should be noted that in the particular embodiment depicted the upward bow in the anterior segment 180 is somewhat higher than the posterior upward bow 186, as seen in FIGS. 14C-14D.

Note that other ring configurations are within the scope of the invention. The ring can be formed from various materials and combinations thereof, such as stainless steel, titanium, Stellite, cloth, etc. The choice of materials and specific design of the ring depend on the particular application. Various ring shapes may be employed. The ring may be relatively flexible or relatively stiff, or may be a combination of stiff and flexible portions.

Figure 15A:
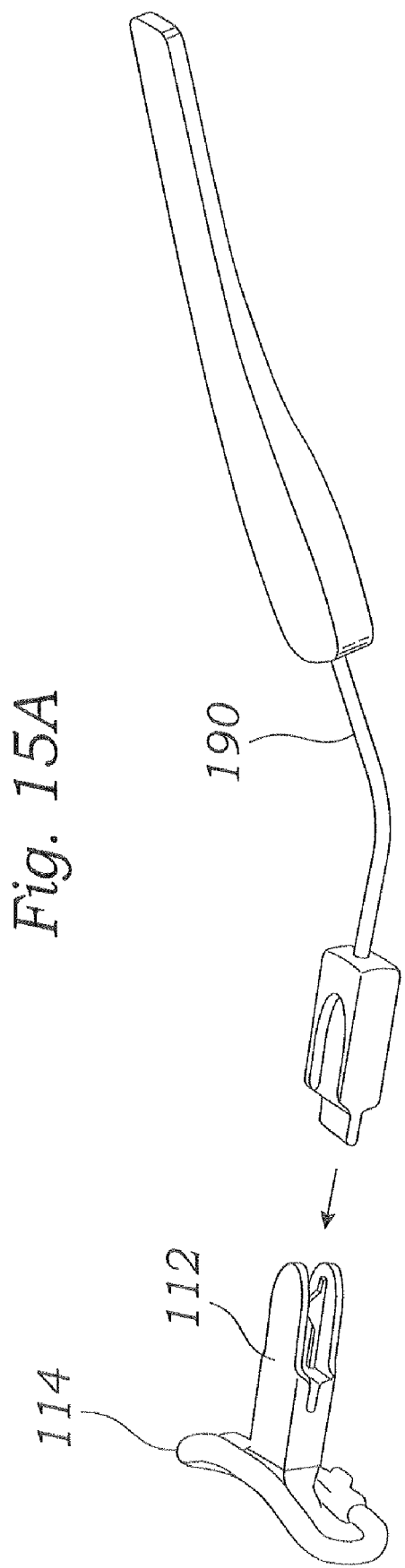
Figure 15B:
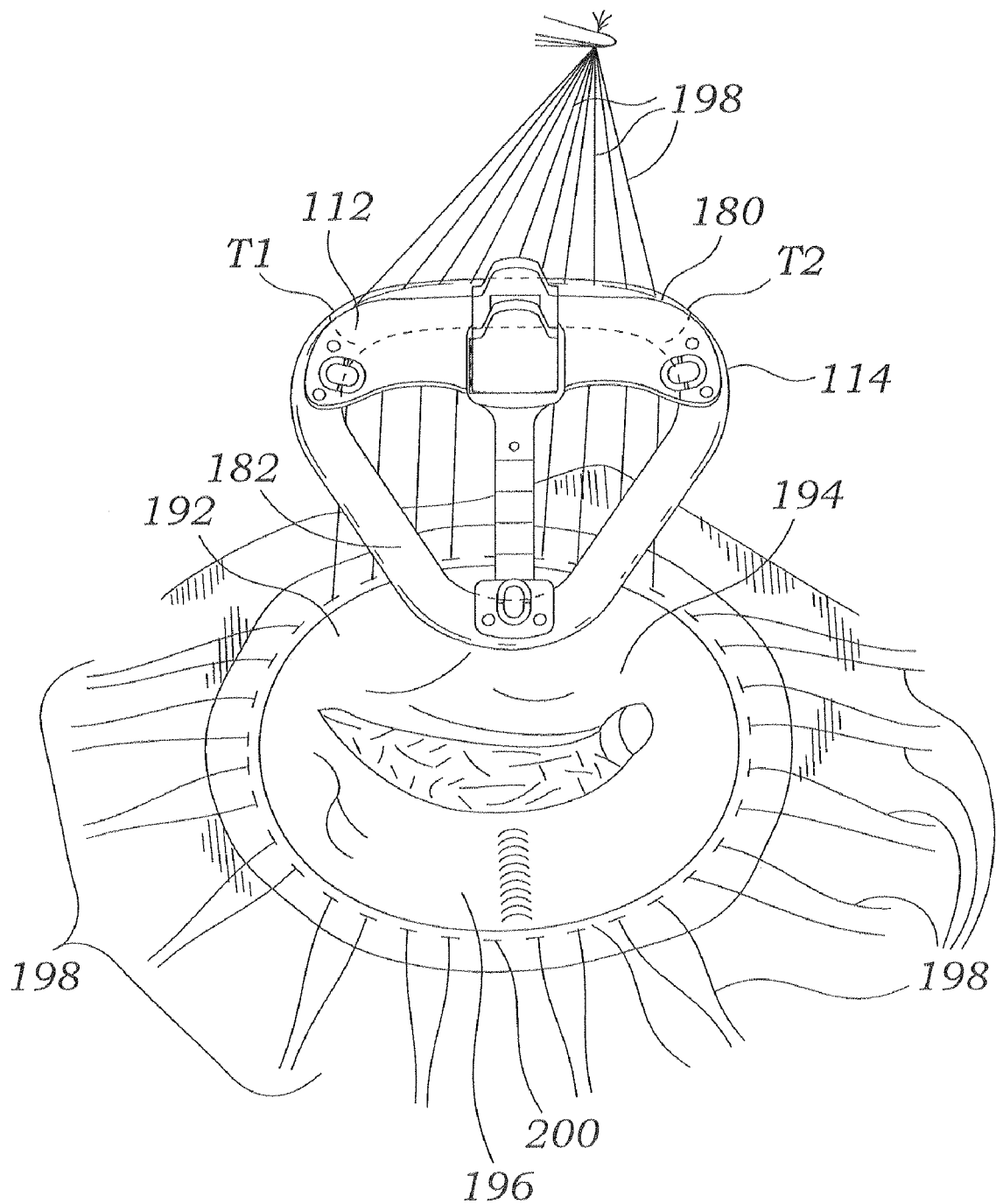

FIGS. 15A-15E depict an implantation procedure using the holder 112 to implant a ring 114 to a heart valve according to the current invention. In FIG. 15A, a handle 190 is depicted being removably secured to the holder 112 and ring 114 combination. FIG. 15B depicts the holder 112 and ring 114 adjacent a heart valve 192 having an anterior leaflet 194 and a posterior leaflet 196. Sutures 198 are passed through the fibrous mitral annulus 200 of the heart valve 192 at a distance of about 2 mm from the leaflet edge. Some of the sutures 198 are also passed through ring 114, and particularly through the anterior portion 180 of the ring 114. Others of the sutures 198 will be passed through the posterior portion 182 of the ring 114, but in the particular embodiment of FIG. 15B this is not depicted as having yet happened. Note that the particular order in which sutures or sets thereof are passed through the ring can vary depending on the particular application, including the preferences of a particular surgeon or other user. For example, a user might pass the posterior-adjacent sutures through the ring first, etc.

Figure 15C:
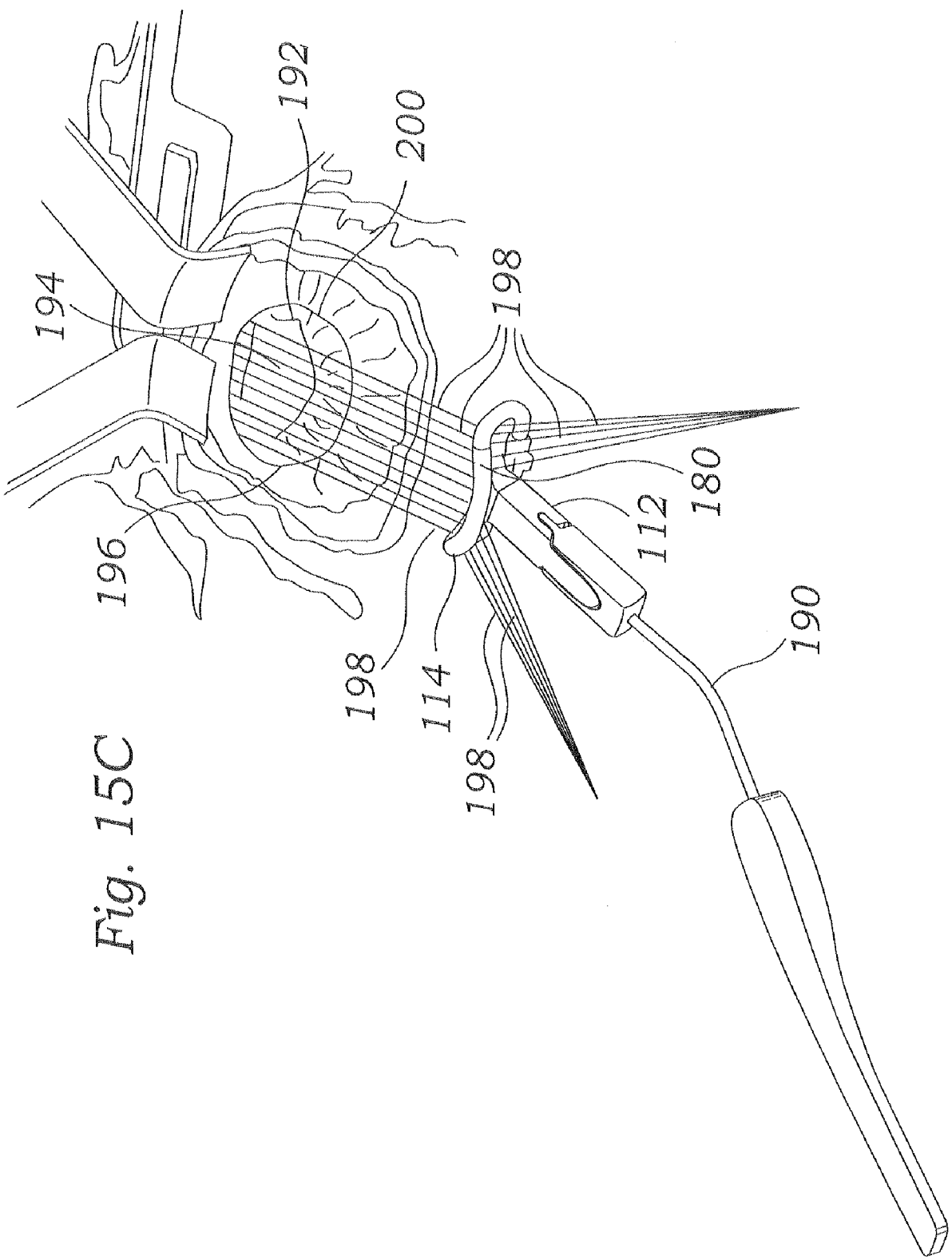

As the operation progresses, all sutures 198 are passed through both the fibrous mitral annulus 200 and the ring 114. In FIG. 15C, the sutures 198 are held in tension while the ring 114 is slid down (sometimes referred to as "parachuting down") the sutures 198 until the ring 114 is seated above the mitral valve 192 and against the mitral valve annulus 200.

Note that in FIGS. 15A and 15C, the handle 190 is depicted removably secured to the holder 112, but in FIG. 15B no handle is depicted. The lack of a handle is FIG. 15B is merely for clarity in the figure, and does not necessarily mean that no handle will be present during that portion of the procedure. Depending on the particular application, including the preference of a particular user, the handle could be left off the holder from the start so that it is not used at all in the procedure. The handle could also be attached to the holder for just one or more parts of the procedure, e.g., the initial passing of the first set of sutures through the ring, or the handle could be attached to the holder throughout the entire procedure.

If the surgeon or other user is satisfied with the initial placement of the ring 114 against the mitral valve annulus 200 (i.e., the placement after the ring 114 is slid down the sutures 198 to the mitral valve annulus 200), the user ties off the sutures 198 in order to tightly secure the ring 114 to the mitral valve annulus 200. As the ring 114 is tightened into place via the sutures 198, the mitral valve annulus 200 is re-shaped to improve coaptation and effectuate the valve repair.

Figure 15D:
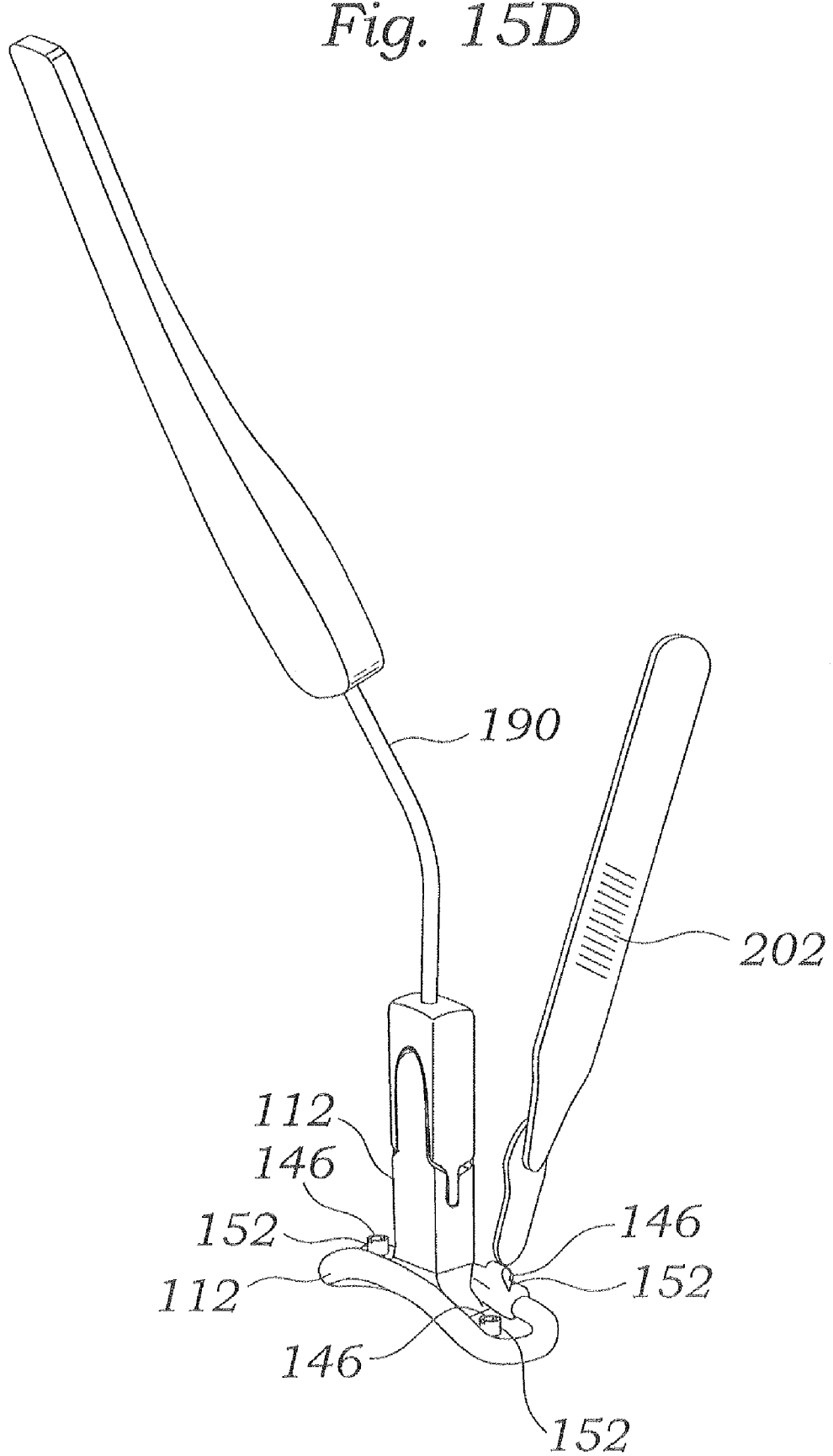

To remove the ring 114 from the holder 112, the user will cut the retaining sutures 152 that hold the ring 114 to the holder 112. A scalpel 202 or other cutting instrument is passed into the cutting wells 146 to cut the retaining sutures 152, as depicted in FIG. 15D. With the retaining sutures 152 cut, the holder 112 can be pulled away from the ring 114. Note that in an exemplary embodiment the retaining sutures 152 are connected via knots or other restraints to the holder 112, so that when the retaining sutures 152 are cut their severed ends will remain connected to the holder 112. Accordingly, when the retaining sutures 152 are cut and the holder 112 pulled away from the ring 114, the retaining sutures 152 will be removed from the ring 114 along with the holder 112.

FIG. 15E depicts the ring 114 secured to the valve annulus 200 and with the holder removed. The sutures 198 have been tied off securely and any excess suture material removed. The heart valve 192 is repaired, with the anterior leaflet 194 and posterior leaflet 196 appearing to have a good coaptation line 204. Valvular competency can be tested by various methods, including methods known in the art such as injecting saline into the left ventricle through the mitral orifice and then verifying whether the coaptation line is visible, regular, and symmetrical. Intraoperative echo can also be used in assessing valvular competency and the quality of the repair.

Note that the ring implantation can be performed in conjunction with other valve repair procedures, such as a quadrangular resection of the posterior leaflet performed to remove excess cusp tissue. For example, in the embodiment depicted in FIG. 15E, the posterior leaflet 196 has been resected, excess tissue removed, and the remaining posterior leaflet portions sutured together, with the resulting leaflet repair suture 206 depicted running through the middle of the posterior leaflet 196.

While the invention has been described with reference to particular embodiments, it will be understood that various changes and additional variations may be made and equivalents may be substituted for elements thereof without departing from the scope of the invention or the inventive concept thereof. For example, while the invention is specifically discussed in application with mitral valve repair, it has applicability in other areas where it is desired to repair valves and similar structures. In addition, many modifications may be made to adapt a particular situation or material to the teachings of the invention without departing from the essential scope thereof. Therefore, it is intended that the invention not be limited to the particular embodiments disclosed herein, but that the invention will include all embodiments falling within the scope of the appended claims.

What is claimed is:

1. An annuloplasty ring and holder assembly combination, comprising:
    an annuloplasty ring configured for placement adjacent a heart valve; and
    a ring holder secured to the annuloplasty ring, the holder comprising:
    a T shaped lower template, including:
    a generally straight and elongated base structure forming a cross bar portion of the T-shaped lower template, the base structure engaging against a first portion of the annuloplasty ring;
    a first radial arm forming a post portion of the T-shaped lower template, the first radial arm extending perpendicularly from a middle of the base structure and across an open middle area to a second portion of the annuloplasty ring, the first radial arm comprising a radial arm engagement surface configured to engage against the second portion of the annuloplasty ring, the template only engaging the annuloplasty ring at the first and second portions thereof.

2. The combination of claim 1, wherein ring encloses a bounded area having a geometric center, the ring further comprises a flow axis, and the base structure extends into the bounded area but does not extend over the geometric center when the geometric center is viewed in plan view parallel to the flow axis.

3. The combination of claim 2, further comprising:
a handle post secured to the base structure, wherein the handle post does not extend over the geometric center when the geometric center is viewed in plan view parallel to the flow axis.

4. The combination of claim 1, wherein the first portion of the annuloplasty ring is an anterior portion of the annuloplasty ring, the anterior portion having a length along a portion of a circumference of the annuloplasty ring, and wherein the base structure extends substantially the entire length of the anterior portion of the annuloplasty ring.

5. The combination of claim 4, wherein second portion of the annuloplasty ring is a posterior portion of the annuloplasty ring, the posterior portion having a length along a portion of a circumference of the annuloplasty ring, and wherein the base structure extends partially along the length of the posterior portion of the annuloplasty ring.

6. The combination of claim 1, wherein the second portion of the annuloplasty ring is a posterior portion of the annuloplasty ring, the posterior portion has a center section, and the radial arm engages against the center section of the posterior portion.

7. The combination of claim 1, wherein the generally straight and elongated base structure extends from one distal end to another and engages the first portion of the annuloplasty ring continuously along an outer edge thereof.

8. The combination of claim 1, wherein the generally straight and elongated base structure extends from one distal end to another and the distal ends curve downward.

9. The combination of claim 1, wherein the ring comprises rigid and flexible portions.

10. An annuloplasty ring and ring holder combination, comprising:
an annuloplasty ring comprising a closed ring body having, in top plan view along the flow axis, a rounded isosceles triangular configuration formed from first, second, and third relatively straight segments which form first, second, and third sides, respectively, of the rounded isosceles triangular configuration; and
a ring holder secured to the annuloplasty ring, the holder comprising a lower template having a generally straight and elongated bar portion engaging against a first relatively straight segment of the annuloplasty ring, and a first radial arm extending radially from the elongated bar portion and terminating in a radial arm distal end engaging against a junction between the second and third relatively straight segments of the annuloplasty ring.

11. The combination of claim 10, wherein the first radial arm extends perpendicularly from a middle of the elongated bar portion.

12. The combination of claim 10, wherein each relatively straight segment has two ends, and the two ends of the second relatively straight segment and of the third relatively straight segment are supported by the holder.

13. The combination of claim 12, wherein each relatively straight segment has a main central portion extending between the two ends, and the second and third relatively straight segments of the annuloplasty ring are generally unsupported by the holder.

14. The combination of claim 10, wherein the first relatively straight segment of the annuloplasty ring is an anterior segment of the annuloplasty ring.

15. The combination of claim 10, further comprising:
a handle post extending upward from the elongated bar portion.

16. An annuloplasty ring and ring holder combination, comprising:
an annuloplasty ring; and
a ring holder comprising:
a handle post;
a first wing extending from handle post in a first direction, the first wing having a distal end and defining a first ring-engaging surface extending from the first wing distal end to the handle post, wherein the first ring-engaging surface engages a first portion of the ring;
a second wing extending from the handle post in a second direction, the second direction being generally opposite to the first direction, the second wing having a distal end and defining a second ring-engaging surface extending from the second wing distal end to the handle post, wherein the second ring-engaging surface engages a second portion of the ring; and
a radial arm extending from the handle post in a third direction and engaging a third portion of the ring, wherein the annuloplasty ring is free of the holder except where engaged by the wings and radial arm.

17. The combination of claim 16, wherein the first portion of the ring comprises a first anterior portion of the ring, and the second portion of the ring comprises a second anterior portion of the ring, and the third portion of the ring comprises a posterior portion of the ring.

18. The combination of claim 16, wherein the ring comprises a first parallel ring body portion that runs generally parallel to the first wing from the first wing distal end to the handle post, and wherein the ring comprises a second parallel ring body portion that runs generally parallel to the second wing from the second wing distal end to the handle post.

19. The combination of claim 16, wherein the first ring-engaging surface extends generally continuously from the first wing distal end to the handle post, and the second ring-engaging surface extends generally continuously from the second wing distal end to the handle post.

20. The combination claim 16, wherein the rounded isosceles triangular annuloplasty ring defines a bounded area having a geometric center, and wherein the elongated bar portion does not extend over the ring geometric center such that the handle post also does not the extend over the geometric center.

* * * * *